(12) United States Patent
Hofenk

(10) Patent No.: US 12,264,347 B2
(45) Date of Patent: Apr. 1, 2025

(54) REPAIR OF UV-INDUCED DNA LESIONS

(71) Applicant: ASTERION THERAPEUTICS BVBA, Antwerp (BE)

(72) Inventor: Jeroen Hofenk, Antwerp (BE)

( * ) Notice: Subject to any disclaimer, the term of this patent is extended or adjusted under 35 U.S.C. 154(b) by 585 days.

(21) Appl. No.: 17/413,792

(22) PCT Filed: Dec. 14, 2019

(86) PCT No.: PCT/EP2019/085208
§ 371 (c)(1),
(2) Date: Jun. 14, 2021

(87) PCT Pub. No.: WO2020/120788
PCT Pub. Date: Jun. 18, 2020

(65) Prior Publication Data
US 2022/0017885 A1    Jan. 20, 2022

(30) Foreign Application Priority Data
Dec. 14, 2018   (EP) .................................... 18212780

(51) Int. Cl.
| | |
|---|---|
| *C12N 9/88* | (2006.01) |
| *A61K 8/66* | (2006.01) |
| *A61K 38/51* | (2006.01) |
| *A61Q 19/08* | (2006.01) |
| *C07K 14/47* | (2006.01) |
| *C12N 15/82* | (2006.01) |

(52) U.S. Cl.
CPC .................. *C12N 9/88* (2013.01); *A61K 8/66* (2013.01); *A61K 38/51* (2013.01); *A61Q 19/08* (2013.01); *C07K 14/47* (2013.01); *C12N 15/8257* (2013.01); *C12Y 401/99003* (2013.01); *C07K 2319/21* (2013.01); *C07K 2319/33* (2013.01)

(58) Field of Classification Search
CPC . C12N 9/88; A61K 8/66; A61K 38/51; A61Q 19/08; A61Q 19/00; C12Y 401/99003; C12Y 401/99013; C07K 2319/00
See application file for complete search history.

(56) References Cited

U.S. PATENT DOCUMENTS

| | | | | |
|---|---|---|---|---|
| 6,046,036 A | * | 4/2000 | Kelley ..................... | C12N 9/93 536/23.4 |
| 2014/0017182 A1 | * | 1/2014 | Trumbore ................ | A61K 8/66 424/59 |

FOREIGN PATENT DOCUMENTS

CN     102247603 A  * 11/2011

OTHER PUBLICATIONS

Tanaka et al. Mutagenesis, 2001, 16, 1-6 (Year: 2001).*
Kanai et al. J. Mol. Biol., 1997, 45, 535-548 (Year: 1997).*
Kanai et al. J. Mol. Evol., 1997, 45, 535-548 (Year: 1997).*
Nakajima et al., "Cloning and Characterization of a Gene (UVR3) Required for Photorepair of 6-4 Photoproducts in *Arabidopsis thaliana*," Nucleic Acids Research, vol. 26, No. 2, Nov. 13, 1997, pp. 638-644.
Tanaka et al., "Effects of Photoreactivation of Cyclobutane Pyrimidine Dimers and Pyrimidine (6-4) Pyrimidone Photoproducts on Ultraviolet Mutagenesis in SOS-Induced Repair-Deficient *Escherichia coli*," Mutagenesis, vol. 16, No. 1, Jan. 31, 2001, pp. 1-6.
Jans et al., "Powerful Skin Cancer Protection by a CPD-Photolyase Transgene," Current Biology, vol. 15, Jan. 26, 2005, pp. 105-115.
"Thermus Thermophilus PHR Gene for DNA Photolyase, Complete DCDS, Sequence: AB064548.2," European Nucleotide Archive, retrieved from https://www.ebi.ac.uk/ena/browser/view/ab064548 on Jul. 13, 2021, 4 Pages.
Search Report from corresponding European Application No. 18212780. 3, Feb. 28, 2019.
International Search Report and Written Opinion from PCT Application No. PCT/EP2019/085208, Mar. 4, 2020.

* cited by examiner

*Primary Examiner* — Thea D'Ambrosio
*Assistant Examiner* — Lioubov G Korotchkina
(74) *Attorney, Agent, or Firm* — Workman Nydegger

(57) ABSTRACT

A composition comprising a recombinant enzyme that comprises a fusion of: a cyclobutane pyrimidine dimer photolyase corresponding to an amino acid encoding sequence having at least 85% sequence identity to SEQ ID NO 1, a pyrimidine(6-4)pyrimidone photolyase corresponding to an amino acid encoding sequence having at least 85% sequence identity to SEQ ID NO 2, and a skin penetrating peptide.

15 Claims, 8 Drawing Sheets

Specification includes a Sequence Listing.

REPAIR OF UV-INDUCED DNA LESIONS

REFERENCE TO SEQUENCE LISTING SUBMITTED ON COMPUTER

The content of the ASCII text file of the sequence listing named "eolf-seg1.txt" which was filed in PCT/EP2019/085208 on Dec. 14, 2019, downloaded from the WIPO database, is 13 kb in size with a created date of May 21, 2021, and electronically submitted via EFS-Web herewith the application, is incorporated herein by reference in its entirety.

FIELD OF THE INVENTION

The invention relates to the field of DNA damage repair, e.g. damage due to ultraviolet radiation, such as in skin protection or skin disease treatment. More specifically it relates to a composition, a nucleic acid molecule and a nucleic acid vector.

BACKGROUND OF THE INVENTION

Deoxyribonucleic acid (DNA), the basic substance of life, changes over the long term in the process of evolution, but strict homeostasis of DNA is important over the short term for the maintenance of individual organisms. DNA damage is thought to occur at the rate of tens of thousands of events daily in each cell, e.g. endogenous DNA damage, while it is carrying out basic activities, such as normal metabolic processes, due to replication errors and oxidative damage. Exogenous factors, such as ultraviolet (UV) light, ionizing radiation, and environmental mutagens (e.g. tobacco smoke, exhaust fumes, etc.) are also known to cause DNA damage.

Chronic excessive exposure to ultraviolet (UV) radiation is one of the most common environmental health hazards that can cause highly toxic effects in most living organisms. The detrimental effects from UV irradiation are currently considered as a major risk factor that contributes to photoaging and the development of skin cancer due to an increased production of cellular reactive oxygen species (ROS), indirect and direct DNA damage, as well as suppressed immune responses.

Absorption of UV light energy by DNA induces various types of lesions. Although single- and double-strand breaks, as well as DNA-protein cross-links, can occur, more than 99% of the UV-induced damage consists of chemical base modifications. In cells that are exposed to UV radiation, photoproducts are formed that are, directly and/or indirectly, involved in premature skin ageing and photocarcinogenesis.

Exposure of DNA molecules to UV light gives rise to reactions between two adjacent pyrimidine nucleobases present in the DNA sequence. These photoinduced reactions lead to the dimerisation of these nucleobases. This affects proper base pairing, which results in interference with key cellular processes like transcription and replication. The resulting species is called a DNA photoproduct or photolesion. Lesions in the DNA can lead to reduction of RNA synthesis, arrest of cell cycle progression, and induction of apoptosis. Moreover, persisting DNA damage can give rise to gene mutations that may allow cells to escape from controlled growth, which may ultimately lead to cancer. These products are highly mutagenic and comprise two major types: the cyclobutane pyrimidine dimer (CPD) and the pyrimidine (6-4)pyrimidone photoproduct (64PP or 6-4PP or (6-4)PP).

Jans et al, in "Powerful skin cancer protection by a CPD-Photolyase transgene," CURRENT BIOLOGY, CURRENT SCIENCE, GB, vol. 15, 2, pp. 105-115, described a protective effect for protection of the skin against UV damage of CPD-photolyase and *Arabidopsis* (6-4) photolyase. Transgenic mice were generated that express both CPD-photolyase and 6-4PP-photolyase to allow rapid light-dependent repair. A construct containing the *Arabidopsis thaliana* 6-4PP photolyase cDNA, preceded by the chicken beta-actin promoter and CMV enhancer, and completed with the 3' part of the human beta-globin gene was used. Transgenic beta-actin-6-4PP-PL mice were bred with beta-actin-CPD-PL mice to obtain double-transgenic animals. The *A. thaliana* 6-4PP photolyase gene has been described by Nakajima et al in "Cloning and characterization of a gene (UVR3) required for photorepair of 6-4 photoproducts in *Arabidopsis* thalania," NUCLEIC ACIDS RESEARCH, INFORMATION RETRIEVAL LTD, vol. 26, 2, pp. 638-644.

Tanaka et al, in "Effects of photoreactivation of cyclobutene pyrimidine dimers and pyrimidine (6-4) pyrimidone photoproducts on ultraviolet mutagenesis in SOS-induced repair-deficient *Escherichia coli*," MUTAGENESIS, vol. 16, 1, pp. 1-6, disclosed treating UV-irradiated pTN89 plasmid with a CPD photolyase, from *E. coli*, and/or a (6-4)PP photolyase, from *A. thaliana*, in vitro, and transfecting the material into SOS-induced *E. coli*.

A cyclobutane pyrimidine dimer is a [2π+2π] cycloaddition between two C5-C6 double bonds of the pyrimidine ring, and gives rise to a species known as the cyclobutane pyrimidine dimer or CPD. In this formation, two pyrimidine rings are bridged together by the four-membered cyclobutane ring. CPD photoproducts account for the majority of the formed pyrimidine dimers after UV irradiation in cells, approximately 80%.

A pyrimidine(6-4')pyrimidone photoproduct (64PP), is a [2π+2π] cycloaddition between the C5-C6 and the C4 carbonyl (imine in the case of cytosine in its keto form) and forms a dimer bridged by a four-membered heterocyle (oxetane for thymine and azetidine for cytosine). This photoreaction between an alkene and a carbonyl group is also called the Paternò-Büchi reaction. The oxetane/azetidine species, being thermodynamically unstable, will split into a structure consisting of two rings connected by a single covalent bond. The 5'-part of the lesion will be a pyrimidine derivative whose C6 position is covalently attached to the C4 position of the 3' pyrimidone. This final product is called the pyrimidine(64)pyrimidone photoproduct or simply the (6-4) photoproduct or (6-4)PP. Although the (6-4)PP is a lesser abundantly formed photoproduct, it is believed to be more cytotoxic than the CPD and may account for approximately 20% of formed lesions.

Exposure to sun rays is the main cause of genetic mutation in skin cells. Every year, millions of people worldwide develop basal and squamous cell carcinomas, which are the two most common skin cancer types. The etiology is related to several factors, including the type of skin and the frequency and exposure index to sun rays. Furthermore, characteristic changes to the skin that are induced by chronic UVA and UVB exposure, referred to as photoaging, are another major concern affecting an even larger population. While a specific subject might not develop skin cancer due to UV induced DNA damage, exposure to UV radiation will cause molecular derangements via photoaging, which eventually leads to premature skin ageing.

The molecular derangements in skin linked to chronic UV exposure have been associated with direct and indirect DNA damage. Ultraviolet B (UVB) (300-320 nm) has long been considered responsible for the skin damage underlying photoaging and skin cancers, whereas the toxicity of UVA (320-400 nm) has been largely overlooked. The intricate molecular derangements of photoaging and photocarcinogenesis remain poorly understood, but UV-induced DNA damage appears to be a major initiating event.

Evidence also suggests that specific molecular derangements—including telomere shortening and the upregulation of proto-oncogenes—may play a role in the setting of UV-induced damage to biological tissues. Telomeres are specialized DNA, made up of a string of repeated TTAGGG, that form chromosome terminators. They protect the ends of chromosomes from enzymatic degradation and are known to shorten after each cell division. The shortening of telomere length has been suggested as a proxy for cellular senescence in the skin.

Remarkably, it has been found that human telomeres are 7-fold hypersensitive to UV-induced DNA damage when compared with coding regions, and removal of CPDs formed in the telomeres is almost absent. Although repeated UV irradiation of diploid fibroblasts did not result in telomere shortening in vitro, little is known about the effects of repeated UV irradiations on human telomeres in cells extracted from skin biopsies.

Telomere length is also important in tumorigenesis. In this regard, a shorter telomere length in basal keratinocytes may trigger chromosomal aberrations that could lead to the development of non-melanoma skin cancers. Skin exposure to UV also results in a significant upregulation in the expression of the proto-oncogene c-FOS, one of the key transcription factors hyperexpressed in human cutaneous cancer. Evidence has also suggested that cultured keratinocytes derived from photodamaged skin hyperexpress c-FOS, which in turn may facilitate the development of skin cancer.

Furthermore, it is known that the development of actinic keratosis is associated and frequently preceded by subclinical disorders in the epidermis surrounding or to surround the actinic keratosis lesion. These subclinical disorders make up the so-called subclinical field cancerization. A high probability for developing actinic keratosis lesions and/or squamous cell cancer has been observed in field cancerization, which is the skin area that shares a genetic risk for developing skin carcinoma due to the damage caused by ultraviolet radiation. It includes areas where the actinic keratosis lesion or non-melanoma skin cancer are already present and show cell damage (e.g. cell atypia) or histological damage (e.g. parakeratosis), but also morphologically normal areas that show at the molecular level the same genetic changes induced by ultraviolet light that characterize squamous cell carcinoma of the skin, e.g. mutations or changes in TP53 gene expression. In the present disclosure, references to 'subclinical field cancerization' refer to the skin area with genetic changes at molecular level induced by ultraviolet light, while in this skin area no clinical evidence of actinic keratosis lesion or non-melanoma skin cancer can be found.

To counteract the deleterious effects of DNA damage produced by UV radiation, all organisms have developed a complex network of repair systems with complementary substrate specificity that keeps the DNA under continuous surveillance. Removal of photolesions from the DNA is performed by the versatile and evolutionary highly conserved nucleotide excision repair (NER) pathway.

NER is a complex multi-step process, and involves the concerted action of about 30 proteins to sequentially execute damage recognition, chromatin remodeling, excision of a small oligonucleotide containing the damage, and gap-filling DNA synthesis followed by strand ligation. The NER system is comprised of two subpathways. Global genome NER (GG-NER) operates genome-wide, but has the disadvantage that certain types of damage (like UV-induced CPDs) are less well recognized and accordingly less efficiently repaired. To prevent such lesions hampering transcription too long by stalling RNA polymerase II, a distinct NER subpathway has evolved, called transcription-coupled repair (TC-NER).

This process directs the repair machinery, preferentially to the blocked polymerase on the template strand of actively transcribed DNA, and operates as a selective backup system for lesions that are slowly, or not at all, repaired by GG-NER.

Many organisms of all kingdoms mount an additional repair system to remove UV lesions called photoreactivation. In contrast to the complex NER pathway, photoreactivation is performed by photolyases that rapidly convert UV lesions back to the original undamaged bases in a simple enzymatic reaction using visible light as an energy source. To perform this reaction, photolyases are equipped with two different chromophoric co-factors. Depending on the photolyase, either 5,10-methyl tetrahydrofolate (MTHF) or 8-hydroxy-5-deazaflavin (8-HDF) serve as light-harvesting antennas that pass on energy to reduced FAD, the chromophore that acts as the reaction center in dimer splitting.

Notably, photolyases show substrate specificity for either CPDs (CPD photolyase) or 6-4PPs (6-4 photolyase). Photolyases occur in bacteria, lower eukaryotes, plants and many animals including marsupials. Remarkably, despite the strong conservation of photoreactivation, this repair mechanism is absent in placental mammals (e.g. humans and mice), implying that photolyase genes have been lost during evolution of this subclass. The inability to photoreactivate CPDs and 6-4PPs leaves placental mammals with only the less efficient NER system for removal of these photolesions.

With the incidence of nonmelanoma skin cancer (NMSC) on the rise, current strategies to prevent skin cancer have been predominantly focused on recommendations for sun avoidance, restricted access of youth to tanning beds, the use of broad spectrum UVA and UVB sunscreens, and application of topical antioxidants. However, these recommendations have not sufficiently diminished the prevalence of NMSC, and development of novel methods to reduce or prevent NMSCs would not only alleviate suffering, but also substantially reduce health care costs.

Since conventional photoprotection strategies are indeed exclusively prophylactic in nature and of no value once DNA damage has occurred, there has been considerable interest in identifying compounds that will prevent, inhibit or reverse the biochemical changes required for premature photoaging and photocarcinogenesis to develop, either by cosmetic or pharmacologic intervention or by dietary manipulation. By targeting different pathways identified as important in the pathogenesis of NMCs, a combination approach with multiple agents or the addition of chemopreventative agents to topical sunscreens may offer the potential for novel and synergistic therapies in treating nonmelanoma skin cancer. An innovative approach to the vexing clinical issue of photoprotection is the topical application of xenogenic DNA repair enzymes.

Two different methods have recently been established: the use of endonuclease and the application of photolyase. The use of endonuclease has been shown to be clinically useful in protecting patients with a nucleotide excision repair defect from premalignant and malignant skin lesions. On the other hand, application of photolyase, a xenogenic enzyme, which has been found in different organisms, is also capable of removing UVB-induced CPDs from normal human skin cells in vivo and appears to be far more effective than endonuclease, and even more effective than the complex, step-wise and ATP-consuming mechanisms of nucleotide excision repair or base repair.

The DNA-repairing mechanism of action of endonuclease differs significantly from that of photolyase. Endonuclease generates a single-stranded incision in DNA at the site of a CPD in a light-independent fashion. The mechanism of incision involves the sequential action of two independent activities of endonuclease: a DNA glycosylase that cleaves the glycosylic bond of the 5'-pyrimidine of a dimer and an apyrimidinic endonuclease that cleaves the phosphodiester bond between the two pyrimidines.

Photolyase, a class of photon-powered nanomachine flavoproteins, depends on a direct reverse repair process called photoreactivation. It uses blue light to repair either one of two types of ultraviolet-induced DNA damage, cyclobutane pyrimidine dimer (CPD) and pyrimidine-pyrimidone (6-4) photoproduct (6-4PP). It thus requires only visible light as an energy source, in which the direct reversal of UV-induced damage is almost instant, as light is absorbed concomitantly with UV radiation causing damage to the DNA.

The photolyase/cryptochrome family consists of 55-70 kD monomeric proteins that contain two non-covalently bound prosthetic groups, flavin adenonucleotide (FAD) and a pterin (or in rare cases, a deazaflavin), and all members of this family share a high degree of sequence identity within their FAD-binding domains.

Photolyases possess a positively charged groove that binds the phosphodiester backbone of DNA and a pocket for binding either cyclobutane pyrimidine dimers or (6-4) photoproducts. The sequence homology between cryptochrome and photolyase in these regions suggests that both enzymes share common structure and chromophore binding and may share a similar mechanism of action, although DNA repair activity of cryptochrome has not been found. Cryptochrome possesses an additional C-terminal tail that extends past the region of homology with photolyase and is believed to be involved in signal transduction and protein—protein interaction. The cyclic electron transfer mechanism utilized by photolyase has been well characterized and may prove to be a basis for uncovering the mechanism behind cryptochrome-mediated phototransduction.

Photolyase family members have no obvious sequence homology to other classes of flavoproteins, perhaps because activated photolyase utilizes flavin in its light-excited state as opposed to flavin oxidoreductase which uses ground-state flavin. Photolyase has persisted throughout evolution and is found in animals, plants, and bacteria. Photolyase is found in organisms as ancient as archaebacteria, and a photolyase gene is even found in certain animal viruses. Cryptochrome has only been identified thus far in plants and animals, excluding *C. elegans*, although putative homologs have been found in bacteria. While the marsupials have retained both photolyase and cryptochrome during evolution, placental mammals only have the cryptochrome, and in the absence of photolyase, UV photoproducts in these latter organisms are removed by the less efficient nucleotide excision repair exclusively. With the diversity of organisms that contain these proteins, the photolyase/cryptochrome family has been classified by three different criteria: function, chromophore composition, and sequence homology.

When classified by function, there are three distinct categories. Approximately 70-80% of DNA photoproducts generated by ultraviolet light are cis,syn-cyclobutane pyrimidine dimers, where a cyclobutane ring is formed between the C5 and C6 carbons of each base. The first functional category, cyclobutane pyrimidine dimer (CPD) photolyase, further referred to as simply 'photolyase', utilizes a cyclic electron transfer to break this bond, resulting in restoration of the natural bases. However, the CPD photolyase cannot repair (6-4) photoproduct lesions. The second functional category relates to a specific enzyme called (6-4) photolyase that specifically binds to and repairs the (6-4) photoproduct. The pyrimidine-pyrimidone (6-4) photoproduct, which comprises 20-30% of total UV-induced photoproducts, is formed through an oxetane intermediate to join C6 of the 5' base to the C4 of the 3' base, with the addition of a hydroxyl group at the C5 of the 5' base. Repair of this adduct cannot be achieved by breaking the (6-4) C—C bond. The (6-4) photolyase presumably stabilizes the oxetane intermediate which is then split by electron transfer to restore the bases. The third functional category relates to cryptochrome. 'Cryptochrome' was originally coined as a generic term to describe plant blue-light receptors which were known to exist but had not been identified for nearly a century. Currently, the term is used to designate photolyase sequence homologs with no DNA repair function but with known or presumed blue-light receptor function. In plants, cryptochromes regulate a variety of growth processes in response to blue-light, and are a significant topic of research in plant biology. However, interest in cryptochromes has dramatically escalated since these pigments may constitute the primary circadian photoreceptor in mammals and possibly other organisms.

Photolyase family members may also be classified by chromophore composition. All photolyases and cryptochromes non-covalently bind the primary chromophore, flavin, within a pocket buried in the folded enzyme. The 'second chromophore', as it is called, acts as a photoantenna and transfers excitation energy to the catalytic FADH-cofactor by fluorescence resonance energy transfer (FRET). The majority of photolyases, all known (6-4) photolyases, and cryptochromes, contain a folate (MTHF) as the second chromophore, referred to as the 'Folate Class'. The 'Deazaflavin Class' represents a handful of CPD photolyases and cryptochromes from those few species which can synthesize the 'ancient molecule' 8-HDH, including *Streptomyces griseus, Anacystis nidulans*, and *Methanobacterium* thermoautotrophicum.

On the basis of sequence homology, two classes were proposed earlier to exist in the photolyase/cryptochrome family which are independent of both function and chromophore composition, Type I and Type II. Type I photolyases include most of the microbial CPD photolyases, all (6-4) photolyases and cryptochromes, while Type II photolyases include CPD photolyases from animals and plants, as well as some microbial photolyases.

It is known in the art to apply to manage field cancerization by a topical application of 5% Imiquimod cream. The application of such cream causes an inflammatory response in the field cancerization, while it does not cause such reaction in normal cells, indicating a specific reaction in impaired cells.

SUMMARY OF THE INVENTION

It is an object of embodiments of the present invention to provide a composition that can efficiently and effectively repair DNA damage induced by ultraviolet radiation, e.g. in the skin.

It is an advantage of embodiments of the present invention that both DNA lesions caused by cyclobutane pyrimidine dimer (CPD) and pyrimidine(6-4)pyrimidone ((6-4)PP) photoproducts can be repaired. While photolyases generally share similar primary sequences and folding structures, a conventional CPD photolyase repairs damage due to its corresponding photoproduct and cannot repair a (6-4)PP lesion and vice versa.

It is an advantage of embodiments of the present invention that a recombinant fusion enzyme is provided that targets both CPD and (6-4)PP photoproducts.

It is an advantage of embodiments of the present invention that photoaging and photocarcinogenesis can be prevented or reduced, e.g. in a subclinical or cosmetic application.

It is an advantage of embodiments of the present invention that a stable enzyme with high specific activity is provided for UV-induced DNA damage.

It is an advantage of embodiments of the present invention that an efficient and high-yield recombinant system is provided that allows to produce industrial amounts of DNA-repair enzymes, e.g. at a high efficiency and/or low cost.

It is an advantage of embodiments of the present invention that a DNA-repair enzyme is provided that can be obtained from a low-cost and highly productive system and in a purified state.

It is an advantage of embodiments of the present invention that a composition for UV-induced DNA damage repair is provided that is safe to administer to living cells.

It is an advantage of embodiments of the present invention that subclinical field cancerization can be reduced, and/or, at least potentially, that existing actinic keratosis lesions and/or non-melanoma skin cancer (NMSC) can be reduced.

It is an advantage of embodiments of the present invention that a DNA-repair enzyme is provided that is specific to UV damage, particularly to both CPD- and 6-4PP photoproducts.

It is an advantage of embodiments of the present invention that a DNA-repair enzyme is provided that has a good stability.

It is an advantage of embodiments of the present invention that a DNA-repair enzyme is provided that is non-cytotoxic and/or non-pyrogenic.

The above objective is accomplished by a method and device according to the present invention.

In a first aspect, the present invention relates to a composition comprising a recombinant enzyme comprising a fusion of a cyclobutane pyrimidine dimer photolyase and a pyrimidine(6-4)pyrimidone photolyase, e.g. the cyclobutane pyrimidine dimer photolyase and the pyrimidine(6-4)pyrimidone photolyase may be jointly included in the recombinant enzyme. The recombinant enzyme, e.g. the fusion, also comprises a skin penetrating enzyme. The cyclobutane pyrimidine dimer photolyase corresponds to an amino acid encoding sequence having at least 85% sequence identity to SEQ ID NO 1, and the pyrimidine(6-4)pyrimidone photolyase corresponds to an amino acid encoding sequence having at least 85% sequence identity to SEQ ID NO 2.

In a composition in accordance with embodiments of the first aspect of the present invention, the skin penetrating peptide may be encoded by the DNA sequence SEQ ID NO 3.

In a composition in accordance with embodiments of the first aspect of the present invention, the recombinant enzyme may be a deazaflavin photolyase.

In a composition in accordance with embodiments of the first aspect of the present invention, the recombinant enzyme may comprise one or more tag peptides to facilitate purification of the recombinant enzyme.

A composition in accordance with embodiments of the first aspect of the present invention may further comprise a carrier and/or an excipient to facilitate uptake of the composition in or on the body.

In a composition in accordance with embodiments of the first aspect of the present invention, the carrier and/or excipient may comprise an encapsulating material for at least temporarily encapsulating at least said cyclobutane pyrimidine dimer photolyase and said pyrimidine(6-4)pyrimidone photolyase, e.g. encapsulating said recombinant enzyme.

In a composition in accordance with embodiments of the first aspect of the present invention, the carrier and/or excipient may comprise a liposome and/or thermoresponsive polyglycerol particles.

A composition in accordance with embodiments of the first aspect of the present invention may comprise a solubilizer, a skin permeation enhancer, a preservative, a moisturizer, a gelling agent, a buffering agent, a surfactant, an emulsifier, an emollient, a thickening agent, a stabilizer, a humectant, a dispersing agent and/or any combination thereof, In a second aspect, the present invention relates to a nucleic acid molecule comprising a first fragment having at least 85% sequence identity to SEQ ID NO: 1, coding for cyclobutane pyrimidine dimer photolyase, and a second fragment having at least 85% sequence identity to SEQ ID NO: 2, coding for a pyrimidine(6-4)pyrimidone photolyase. For example, the nucleic acid molecule may comprise a first fragment (substantially) corresponding to SEQ ID NO: 1, coding for cyclobutane pyrimidine dimer photolyase, and a second fragment (substantially) corresponding to SEQ ID NO: 2, coding for a pyrimidine(6-4)pyrimidone photolyase.

A nucleic acid molecule in accordance with embodiments of the second aspect of the present invention may comprise a third fragment having at least a 85% sequence identity to SEQ ID NO: 3, e.g. (substantially) corresponding to SEQ ID NO:3.

A nucleic acid molecule in accordance with embodiments of the second aspect of the present invention may comprise a His-tag for facilitating purification.

In a third aspect, the present invention relates to a nucleic acid vector comprising a nucleic acid molecule in accordance with embodiments of the second aspect of the present invention and transcription and translation control sequences effective to initiate transcription and subsequent protein synthesis in a host cell.

A nucleic acid vector in accordance with embodiments of the third aspect of the present invention may have at least a 85% sequence identity to SEQ ID NO:4, e.g. may have at least a 90% sequence identity to SEQ ID NO:4, e.g. may have at least a 95% sequence identity to SEQ ID NO:4, e.g. may be substantially identical to SEQ ID NO:4, e.g. may be identical to SEQ ID NO:4.

In a nucleic acid vector in accordance with embodiments of the third aspect of the present invention the host cell may be a *Nicotiana Benthamiana* cell.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
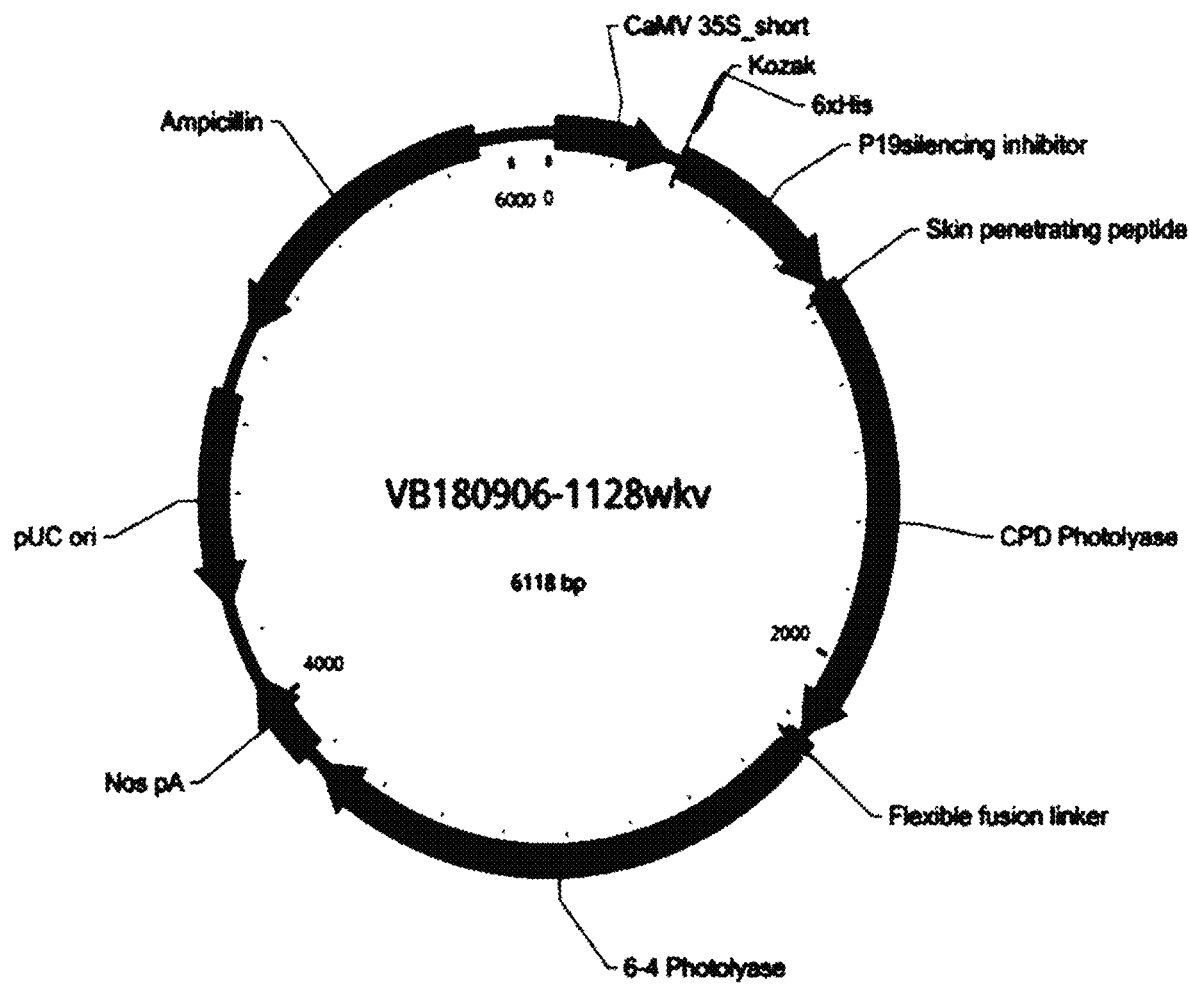
FIG. 1 shows a vector construct, pPRP[Exp]-CaMV35S-rPhotolyase, in accordance with embodiments of the present invention.

The drawings are only schematic and are non-limiting. In the drawings, the size of some of the elements may be exaggerated and not drawn on scale for illustrative purposes.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof.

Reference throughout this specification to "one embodiment" or "an embodiment" or "embodiments" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

In a first aspect, the present invention relates to a composition that comprises a cyclobutane pyrimidine dimer photolyase encoded by the DNA sequence SEQ ID NO: 1, as detailed in the sequence listing enclosed with the present application, or a homologous sequence that has a minimum of 15% sequence identity to SEQ ID NO: 1. Thus, the cyclobutane pyrimidine dimer photolyase corresponds to an amino acid encoding sequence having at least 85% sequence identity to SEQ ID NO: 1. The sequence SEQ ID NO: 1 may correspond to the coding sequence of Deoxyribodipyrimidine photolyase from *Thermus Thermophilus*, e.g. the cyclobutane pyrimidine dimer photolyase may correspond to the full length Deoxyribodipyrimidine photolyase (CPD) protein from *Thermus Thermophilus*, codon optimized for *Nicotiana Benthamiana* species.

The composition comprises a pyrimidine(6-4)pyrimidone photolyase encoded by the DNA sequence SEQ ID NO: 2 or a homologous sequence that has a minimum of 15% sequence identity to SEQ ID NO: 2. Thus, the pyrimidine (6-4)pyrimidone photolyase corresponds to an amino acid encoding sequence having at least 85% sequence identity to SEQ ID NO: 2. The sequence SEQ ID NO: 2 may correspond to the coding sequence of (6-4) photolyase from *Arabidopsis Thaliana*, e.g. the pyrimidine(6-4)pyrimidone photolyase may correspond to the full length (6-4) Photolyase protein from *Arabidopsis Thaliana*, codon optimized for *Nicotiana Benthamiana* species.

Thus, the composition comprises the combination, by fusion, of the cyclobutane pyrimidine dimer photolyase and the pyrimidine(6-4)pyrimidone photolyase.

Constructs for N- and C-terminally truncated and both N- and C-terminally truncated versions of both nucleotide sequences and all homologous coding sequences, with a minimum of 15% sequence identity, are also considered within the scope of the present invention.

The cyclobutane pyrimidine dimer photolyase and the pyrimidine(6-4)pyrimidone photolyase, which may be conjugated in a single DNA repair enzyme, as detailed further hereinbelow, can advantageously repair DNA damage caused by exposure to ultraviolet light (UV). These enzyme mechanisms require visible light, preferentially from the violet/blue end of the spectrum, known as photoreactivation. Photolyases bind complementary DNA strands and break certain types of pyrimidine dimers that arise when a pair of thymine or cytosine bases on the same strand of DNA becomes covalently linked. These dimers result in a bulge of the DNA structure, referred to a lesion. Photolyases have a high affinity for these lesions and reversibly bind and convert them back to the original bases. Depending on the cofactor which is used during the DNA reparation, photolyases are classified into folato photolyases if they use flavin and folate as cofactors or deazaflavin photolyases if the use flavin and deazaflavin as cofactors.

In embodiments of the present invention, the composition further comprises a skin penetrating peptide, e.g. may comprise a skin-penetrating domain (Keratin Binding Peptide, KBP), e.g. to facilitate delivery trough the stratum corneum into human skin cells.

The skin penetrating peptide may be encoded by the DNA sequence SEQ ID NO: 3, or a homologous sequence thereof. Thus, the skin penetrating peptide may correspond to an amino acid encoding sequence having at least 85% sequence identity to SEQ ID NO: 3. This sequence may be codon optimized for *Nicotiana Benthamiana* species.

However, in embodiments in accordance with the present invention, another cell- and/or skin penetrating peptide, e.g. as known in the art, may equally be used. Such peptide, e.g. the aforementioned peptide in accordance with SEQ ID NO:3 or another suitable peptide, is incorporated into a recombinant photolyase fusion enzyme comprising these photolyases.

The skin penetrating peptide may be fused with, e.g. conjugated to, the cyclobutane pyrimidine dimer photolyase to enable a good penetration of the stratum corneum, such as to enable the repair of DNA lesions produced by Cyclobutane Pyrimidine (CPD) photoproducts.

The skin penetrating peptide, or a further skin penetrating peptide, may be fused with, e.g. conjugated to, the pyrimidine(6-4)pyrimidone photolyase to enable a good penetration of the stratum corneum, such as to enable the repair of DNA lesions produced by 6-4 Pyrimidine-Pyrimidone (6-4PP) photoproducts.

In a preferred embodiment, the composition comprises a recombinant enzyme, i.e. a recombinant photolyase fusion enzyme, comprising a fusion of the cyclobutane pyrimidine dimer photolyase and the pyrimidine(6-4)pyrimidone photolyase. Such engineered recombinant DNA-repair photolyase fusion enzyme of the CPD Photolyase and the 6-4PP Photolyase may be transiently expressed by wild-type *Nicotiana Benthamiana* plants. Thus, the recombinant enzyme may comprise or consist of a conjugation of the cyclobutane pyrimidine dimer photolyase and the pyrimidine(6-4)pyrimidone photolyase. The recombinant enzyme may thus be encoded by a sequence comprising the two catalytic nucleotide sequences SEQ ID NO: 1 and SEQ ID NO: 2, or homologs thereof.

In an embodiment of the present invention, the recombinant photolyase fusion enzyme is a deazaflavin photolyase.

The recombinant enzyme may also comprise, e.g. in said fusion, the skin penetrating enzyme, e.g. the exemplary skin penetrating enzyme in accordance with SEQ ID: 3.

Protein linkers may be incorporated into the primary structures of the recombinant photolyase fusion enzyme, for aiding in the fusion of two or more protein sequences, e.g. the sequences SEQ ID NO:1, SEQ ID NO:2 and/or SEQ ID NO:3, or a combination thereof. Such protein linkers may include flexible linkers, rigid linkers, in vivo cleavable linkers, among others.

The recombinant enzyme may also comprise one or more tag peptides, e.g. engineered into the primary structures of the recombinant photolyase fusion enzyme, to facilitate purification of recombinant enzyme. The tag peptide(s) may consist of any one, or any combination, of the following: a polyhistidine tag, a streptavidin (biotin-binding) tag, a flagellar antigen tag, a hemagglutinin tag, or a glutathionine S-transferase tag, among others.

Transient expression of the recombinant fusion enzyme in *Nicotiana Benthamiana* plants may advantageously enable a high throughput platform to produce the compound at industrial scale and/or at a low cost. However, embodiments of the present invention are not necessarily limited thereto, e.g. any other suitable expression host may equally be used, including but not limited to, bacteria, yeast, insect, mammalian, or other plant expression systems.

For example, FIG. 1 illustrates an exemplary vector construct of a recombinant enzyme for use in a composition in accordance with embodiments of the present invention.

The vector sequence of this exemplary vector construct is included in SEQ ID NO:4. This exemplary vector of 6118 bp is a plant regular plasmid gene expression vector suitable for a cloning host Stb13 or alternative strain, with antibiotic resistance to ampicillin. The vector components are, in order, a cauliflower mosaic virus 35S promoter, a Kozak translation initiation sequence, a P19 silencing inhibitor, a 6×His tag, the skin penetrating peptide as discussed hereinabove in accordance with SEQ ID NO:3, the CPD photolyase as discussed hereinabove in accordance with SEQ ID NO:1, a flexible fusion linker, the 6-4 photolyase as discussed hereinabove in accordance with SEQ ID NO:2, a nopaline synthase polyadenylation signal, a pUC origin of replication, and an ampicillin resistance gene (ORF).

The composition, in accordance with embodiments of the present invention, may consist of the recombinant photolyase fusion enzyme in a highly purified form, e.g. with the proviso that no additional protein components are present in the composition. However, in other embodiments of the present invention, the compositon may comprise additional components, as briefly discussed hereinbelow, e.g. to form a readily applicable pharmaceutal or cosmetic composition.

The percentage by weight of the recombinant photolyase fusion enzyme in the composition may be in the range of 0.00001% to 99.99999%, e.g. in the range of 0.0001% to 99.9999%, e.g. in the range of 0.001% to 99.999%, e.g. in the range of 0.01% to 99.99%, e.g. in the range of 0.1% to 99.9%, e.g. in the range of 1% to 99%.

In an embodiment of the present invention, the percentage by weight of the recombinant photolyase fusion enzyme in the composition is about 0.001%. about 0.01%, about 0.02%, about 0.03%, about 0.04%, about 0.05%, about 0.06%, about 0.07%, about 0.08%, about 0.09%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 15%, about 20%, about 25%, about 30%, about 35%, about 40% about 45%, about 50%, about 55%, about 60%, about 65%, about 70%, about 75%, about 80%, about 85%, about 90%, about 95%, about 99% or more.

The composition may also comprise a carrier, e.g. a pharmaceutically acceptable carrier, carrier and/or an excipient to facilitate uptake of the composition in or on the body. The carrier and/or the excipient may comprise or consist of a non-toxic filler material. The carrier and/or the excipient may comprise a diluent.

The carrier and/or the excipient may comprise an encapsulating material for at least temporarily encapsulating said the recombinant enzyme.

The carrier and/or the excipient may comprise an encapsulating material for at least temporarily encapsulating the cyclobutane pyrimidine dimer photolyase and the pyrimidine(6-4)pyrimidone photolyase.

The carrier and/or the excipient may comprise an encapsulating material for at least temporarily encapsulating the cyclobutane pyrimidine dimer photolyase and the pyrimidine(6-4)pyrimidone photolyase and the skin penetrating enzyme.

The carrier and/or the excipient may comprise liposome and/or thermoresponsive, e.g. dendritic, polyglycerol particles.

Suitable cosmetic or pharmaceutical carriers include any such materials known in the art, e.g., any liquid, gel, solvent, liquid diluent, solubilizer, polymer or the like, which is nontoxic and which does not significantly interact with other components of the composition or the skin in a deleterious manner.

Suitable skin permeation enhancers are well known in the art and include lower alkanols, such as methanol ethanol and 2-propanol; alkyl methyl sulfoxides such as dimethylsulfoxide (DMSO), decylmethylsulfoxide (C10 MSO) and tetradecylmethyl sulfoxide; pyrrolidones, urea; N,N-diethyl-m-toluamide; C2-C6 alkanediols; dimethyl formamide (DMF), N,N-dimethylacetamide (DMA) and tetrahydrofurfuryl alcohol, among others.

The composition may also comprise a solubilizer, a skin permeation enhancer, a preservative, a moisturizer, a gelling agent, a buffering agent, a surfactant, an emulsifier, an emollient, a thickening agent, a stabilizer, a humectant, a dispersing agent and/or any combination thereof.

Examples of solubilizers include, but are not limited to, hydrophilic ethers such as diethylene glycol monoethyl ether (ethoxydiglycol, available commercially as Transcutol®) and diethylene glycol monoethyl ether oleate (available commercially as Softcutol®); polyoxy 35 castor oil, polyoxy 40 hydrogenated castor oil, polyethylene glycol (PEG), particularly low molecular weight PEGs, such as PEG 300 and PEG 400, and polyethylene glycol derivatives such as PEG-8 caprylic/capric glycerides (available commercially as Labrasol®); alkyl methyl sulfoxides, such as DMSO; pyrrolidones, DMA, and mixtures thereof.

The composition may be suitable for topical application. The composition may be used in a subclinical or cosmetic setting for the prevention and/or treatment of photoaging, photocarcinogenesis, actinic keratosis, xeroderma pigmentosum, and (non-melanoma) skin cancer.

The composition may be a medicament, or used in a medicament. The composition may be used as a cosmetic ingredient.

In a second aspect, the present invention relates to a composition in accordance with embodiments of the first aspect of the present invention for use in a medicament.

Embodiments of the present invention may relate to a composition in accordance with embodiments of the first aspect of the present invention for use in a medicament for topical application, e.g. for administration on the skin and/or mucosa.

Embodiments of the present invention may relate to a composition in accordance with embodiments of the first aspect of the present invention for use in a medicament for oral, mucosal or subcutaneous administration.

Embodiments of the present invention may relate to a composition in accordance with embodiments of the first aspect of the present invention for use in a medicament or cosmetic for the treatment and/or prevention of photoaging, photocarcinogenesis and/or epithelial tissue diseases and/or disorders, e.g. of actinic keratosis, xeroderma pigmentosum, and/or (non-melanoma) skin cancer.

Embodiments of the present invention may relate to a composition in accordance with embodiments of the first aspect of the present invention for use in a cosmetic composition, such as a cream or lotion, for preventing photocarcinogenesis and/or photoageing.

Embodiments of the present invention may relate to a composition in accordance with embodiments of the first aspect of the present invention for use in a cosmetic composition, such as a cream or lotion, or a medicament to reduce skin damage by ultraviolet light or chemical agents which cause DNA distortion.

Embodiments of the present invention may relate to a composition in accordance with embodiments of the first aspect of the present invention for use in a medicament for the treatment of a cancerization field in a patient with actinic keratosis, xeroderma pigmentosum, and/or (non-melanoma) skin cancer.

For example, a risk of developing actinic keratosis lesions and/or non-melanoma skin cancer (NMSC) in human subjects having a subclinical cancerization skin field may be advantageously reduced by embodiments of the present invention. A composition in accordance with embodiments of the present invention may be topically applied on the skin field cancerization of the patient. For example, such skin field cancerization may be characterized by increased expression levels of TP53, p21 and/or PCNA, and/or decreased expression levels of CPI-17 with respect to the expression levels in healthy skin.

For example, aging of the skin due to exposure to UV, for example, due to tanning and/or sunburn, or due to exposure of to a mutagenic compound such as a DNA intercalating agent, a DNA methylating agent, including occupational exposure, herein termed as photoaging and photocarcinogenesis, may be reduced. A composition in accordance with embodiments of the present invention may be topically applied. The composition may comprise as the active ingredient an amount of the recombinant fusion enzyme together with a skin- or cell penetrating peptide (either as a separate molecule or as part of a fusion protein construct), and a carrier acceptable and useful for topical application of a protein. Topical administration forms include, but are not limited to, serums, sprays, ointments, creams, emulsions, lotions, gels, or sunscreen. Various additives, known to those skilled in the art, may be included in the topical formulations of the invention. Examples of additives include, but are not limited to, solubilizers, skin permeation enhancers including encapsulation methods, preservatives (e.g., anti-oxidants), moisturizers, gelling agents, buffering agents, surfactants, emulsifiers, emollients, thickening agents, stabilizers, humectants, dispersing agents and cosmetic or pharmaceutical carriers.

Embodiments of the present invention enable a method for cleaving DNA molecules at positions with structural distortions, wherein the DNA can be cleaved in the vicinity of the distortion by a stable recombinant fusion photolyase protein as detailed hereinabove. The structural distortion can result from mismatch at the site of the distortion in a single-stranded (ssDNA) or double-stranded (dsDNA) DNA molecule, from UV damage. Cumulative damage to DNA can result in an unattractive and aged appearance of the skin, especially on the face, neck and chest, if that damage is not repaired, the present invention can be supplied to the skin in substantially pure form for in vitro reactions, or they can be supplied for in vivo reactions, including but not limited to compositions for topical application (in the form or of an ointment, salve, cream, lotion, liquid or transdermal patch) in compositions for topical administration, with the result that damage to skin cells is reduced and the apparent aging of the skin is reduced. The damage caused by CPD and (6-4) photoproducts in ssDNA as well as dsDNA can be repaired, with the result that skin damage resulting from distorted DNA structures and mutagenesis is reduced.

In another aspect of the present invention, embodiments relate to nucleic acid molecules encoding polypeptide fragments corresponding to SEQ ID NO: 1 and SEQ ID NO: 2, and optionally also SEQ ID NO:3, or homologs thereof, and recombinant cells, tissues and animals containing such nucleic acids or polypeptide fragments, antibodies to the polypeptide fragments, assays utilizing the polypeptide fragments, pharmaceutical and/or cosmetic preparations containing the polypeptide fragments and methods relating to all of the foregoing.

A nucleic acid molecule in accordance with embodiments of the present invention may comprise a first fragment having at least 85% sequence identity to SEQ ID NO: 1, coding for a cyclobutane pyrimidine dimer photolyase, and a second fragment having at least 85% sequence identity to SEQ ID NO: 2, coding for a pyrimidine(6-4)pyrimidone photolyase. The nucleic acid molecule may further comprise a third fragment having at least a 85% sequence identity to SEQ ID NO: 3. The nucleic acid molecule may further comprise a tag, e.g. a His-tag, for facilitating affinity purification.

In yet another aspect, the invention relates to a nucleic acid vector the nucleic acid molecule in accordance with embodiments of the previous aspect of the invention described hereinabove, and transcription and translation control sequences effective to initiate transcription and subsequent protein synthesis in a host cell.

FIG. 1 illustrates such vector construct, pPRP[Exp]-CaMV35S-rPhotolyase, in accordance with embodiments of the present invention.

The nucleic acid vector may comprise a nucleotide sequence encoding Deoxyribodipyrimidine photolyase from *Thermus Thermophilus*, e.g. SEQ ID NO:1, and the coding sequence of (6-4) photolyase from *Arabidopsis Thaliana* or co-expression of His-tag and/or skin penetrating peptide sequence and transcription and translation control sequences effective to initiate transcription and subsequent protein synthesis in a host cell. Where a His-tagged version of the present invention is expressed, the His tag portion is desirably removed (preferably after affinity purification but also any other appropriate purification method) by protease cleavage, for example using thrombin, but the presence of the His-tag does not negatively impact activity, skin penetration (in the case of the embodied skin penetrating sequence or other skin/cell penetration peptide fusion proteins) or stability during storage.

The novel engineered recombinant photolyase fusion enzyme described hereinabove reduces DNA damage caused by UV radiation and consequently increases human skin cell survival to UV exposure. Accordingly, this agent can advantageously be used for the reduction in the extent or risk of and/or prevention of human skin cancer and skin photoaging caused by sunlight exposure. The engineered proteins of the present invention can be formulated into cosmeceutical as well as pharmaceutical products.

A potential limitation for the use of any pyrimidine dimer-specific DNA glycolase (pdg) is that their substrate specificities do not include recognition of 6-4PPs. However, the composition in accordance with embodiments of the present invention has a very broad substrate specificity which includes both CPDs and 6-4PPs.

Surprisingly it was found that the characteristics of a recombinant fusion enzyme in accordance with embodiments of the present invention, together with easy obtention processes, purification and stability, makes it an adequate molecule for the development of a technology to be applied in enzymatic therapy in the subclinical and/or cosmetic field.

A large quantity of biochemically modified, active recombinant photolyase fusion protein, highly purified in *Nicotiana Benthamiana* plants, can be obtained. To facilitate delivery of purified recombinant photolyase fusion protein through the stratum corneum, into human skin cells, a skin-penetrating peptide (Keratin Binding Peptide, KBP) may be fused to the N-terminus. To facilitate rapid, simple purification of the recombinant photolyase fusion protein, a 6×His tag, also known as polyhistidine tag, His6 tag and/or hexa histidine tag, may be attached to the N-terminus of the protein. We have demonstrated that the recombinant photolyase fusion enzyme is enzymatically active.

*Nicotiana benthamiana* (*N. benthamiana*) is a particularly suitable bioreactor for the transient expression of recombinant protein in a manufacturing setting. The small ornamental plant has a high leaf to stem ratio and is very prolific in hydroponic culture. *N. benthamiana* tolerates the transfection vectors and delivers maximum synthesis of heterologous proteins in 5-7 days after transfection. Scale-up of this bioreactor is a matter of growing more plants, not re-engineering processes.

Plants have all the eukaryotic cell machinery to accurately produce human and animal proteins. Thus, the bioreactor is the individual plant. Plants are well suited to express complex proteins such as monoclonal antibodies, and minimize risk by not supporting growth of human or animal pathogens.

For all agroinfiltration experiments, discussed hereinbelow, 5- to 7-weeks-old N. benthamiana plants were used.

N. Benthamiana seeds were grown in a greenhouse. Seedling and germination of N. benthamiana plants were carried out under LED illumination 24 h/day, 7 days/week. Red and blue diodes were selected that match the action spectrum of photosynthesis (25% blue and 75% red). Other wavelengths were not productive. The LED's were focused on the plants. Plants grown to usable maturity 20% faster in this system as compared to other commercial solutions. All seeds were germinated using identical soil and fertilizer at 26.6° C.

For the biosynthesis of the genes of interest, Two genes; Thermus thermophilus (strain HB8/ATCC 27634/DSM 579) PhR gene (Uniprot: P61497, version 95, Jun. 7, 2017), Arabidopsis Thaliana UVR3 gene (Uniprot: O48652, version 101, Oct. 25, 2017), skin penetrating peptide sequence (AACSSSPSKHCGG), and a flexible fusion linker (GGGGSGGGGSGGGGS) were used as a template to biosynthesize the novel engineered recombinant fusion enzyme. The restriction sites for EcoRI and BglII were added to the 5' and 3' ends of the gene, respectively. Codon usage was optimized and the gene synthesis was done by Genscript Inc. The entire 2859 bp fragment was cloned into pUC57 vector to facilitate gene subcloning into plant expression vector. See FIG. 1 for a vector map and the enclosed nucleotide sequences SEQ ID NO: 1, SEQ ID NO:2 and SEQ ID NO:3.

As the native PhR and UVR3 genes employs tandem rare codons and could reduce the efficiency of translation or even disengage the translational machinery, the codon usage bias in N. Benthamiana was used by upgrading the codon adoption index (CAI) from 0.70 to 0.88. The GC content and unfavourable peaks have been optimized to prolong the half-life of the mRNA. The Stem-Loop structures, which impact ribosomal binding and stability of mRNA, were broken. In addition, negative cis-acting sites were screened and successfully modified.

For the construction of plant expression vector, the entire 2859 bp-fragmental-orf was excised from pUC57-rPhotolyase by digesting with both EcoRI and BglII and subcloned into pPRP[Exp]-CaMV35S binary vector in the corresponding sites and under the control of 35S-promoter. The transformed colonies were confirmed by restriction digestion. The recombinant plasmid pCambia-PhR/UVR3 was extracted from the selected colony and consequently was transformed into Agrobacterium to carry out agroinfilteration experiments.

The pPRP[Exp]-CaMV35S-PhR/UVR3 construct was transformed into Agrobacterium tumefaciens (A. tumefaciens) strains GV3101 C58C1 and LBA4404 and wild-type strains A4, At06, At10, and At77 using electroporation technique at 2.5 kV, 25 mF and 400Ω. The transformed cells were plated on LB agar medium containing 50 mg/ml Ampicillin (Sigma Aldrich).

Agroinfiltration was used for transient expression in N. Benthamiana with A. tumefaciens. strains as previously described. 100 µl of transformed Agrobacterium frozen cells stock was inoculated in 5 ml LB broth (Thermo Fisher Scientific) and supplemented with 50 mg/ml Ampicillin. Overnight, the culture was incubated at 28° C., shaking at 220 rpm. 500 µl was used to inoculate 50 ml of LB medium. The cultural cells were incubated at 28° C. shaking at 220 rpm until the culture had reached an O.D.600=0.6. The cells were harvested by centrifugation at 6000 rpm and resuspended in 50 ml MES buffer (10 mM MES; pH 5.5, 10 mM $MgCl_2$). This mixture was incubated for 2.5 hours at room temperature with 120 µM acetosyringone and was added to the Agrobacterium suspension in infiltration buffer (1× MS, 10 mM MES, 2.5% glucose). For the effect of monosaccharide on induction of vir gene, different percentages of glucose (0, 1, 2 or 4%) were added to the Agrobacterium suspension in the infiltration buffer (1× MS, 10 mM MES, 200 µM acetosyringone). 5- to 7-weeks old N. benthamiana plants were infiltrated in a vacuum chamber by submerging N. Benthamiana plant aerial tissues in Agrobacterium suspension and applying a 50-400 mbar vacuum for 30, 45 or 60 seconds.

The most optimal infiltration was routinely applied at 50-100 mbar for 60 sec. Once the vacuum was broken, infiltrated N. Benthamiana plants were removed from the vacuum chamber, thoroughly rinsed in water, and grown for 5-7 days under the same growth conditions used for pre-infiltration growth. To avoid any variability, the leaves and location on the leaf, comparably-sized leaves for each plant of similar age were agro-infiltrated for each experiment.

Figure 2:
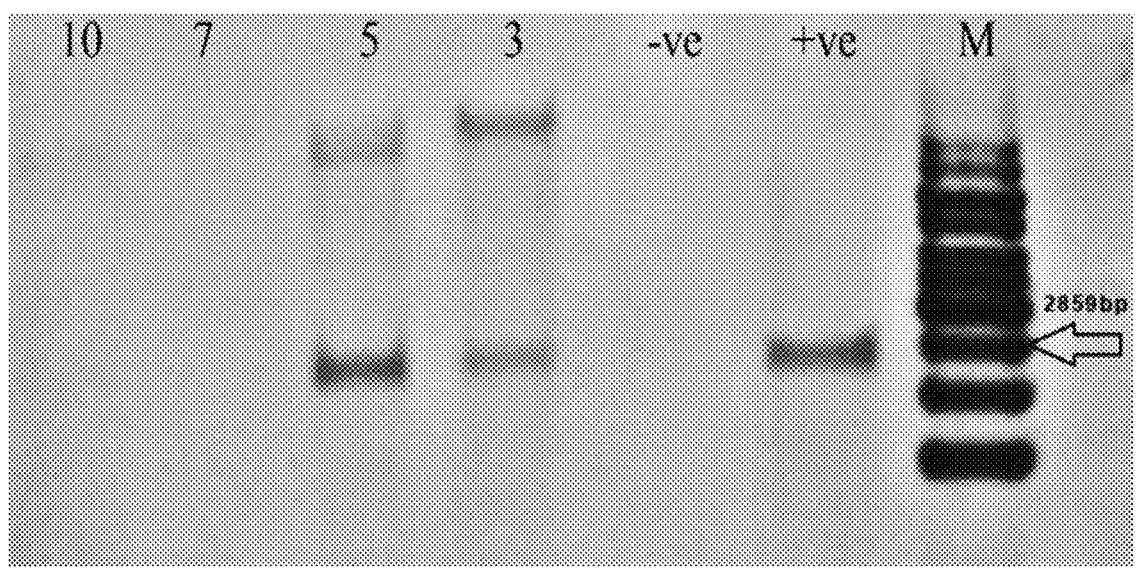
FIG. 2 shows Southern Blot results using PhR/UVR3 probe for the total DNA of PhR/UVR3-infiltrated *N. Benthamiana*, in an example for illustrating embodiments of the present invention.

For the Southern Blot Analysis, individual agroinfiltrated leaves with the pPRP[Exp]-CaMV35S-PhR/UVR3 construct were harvested at different time-intervals; 4, 6, 8 and 10 days post-infiltration, in addition to un-infiltrated plants were used as control. DNA of infiltrated leaves was extracted by DNeasy Plant DNA mini kit (QIAGEN) and fragmented by endonuclease enzyme; EcoRI. The recombinant 2859 bp-fragmental-orf released from pUC57-rPhotolyase was used as a probe. Labeling and detection were carried out using Biotin Deca Label DNA Labeling Kit (Thermo Fisher Scientific) and Biotin chromogenic Detection kit (Thermo Fisher Scientific) respectively. (See FIG. 2)

Figure 3:
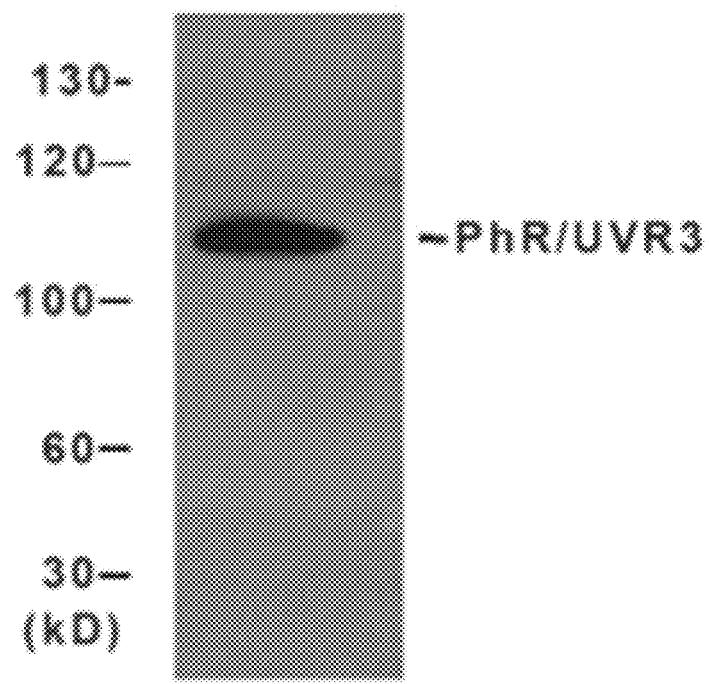
FIG. 3 shows Western Blot results for PhR/UVR3 infiltrated into *N. Benthamiana*, in an example for illustrating embodiments of the present invention.

For the Western Blot Analysis, individual agroinfiltrated N. Benthamiana leaves were harvested and grinded in liquid nitrogen. Total proteins were extracted using SDS-extraction buffer (2% SDS, 0.2% bromopheol blue, 10% glycerol), and the extracts were clarified by centrifugation at 14,500 g for 20 min at 4° C. The, supernatants were transferred to fresh tubes, and the protein content was determined (Bradford assay—1976). Total proteins (40 µg) were separated by SDS-PAGE and then transferred onto polyvinylidene difluoride (PVDF) membranes. Polyvinylidene difluoride membranes were blocked for at least 2 hours and then probed with rabbit anti-CPD photolyase and rabbit anti-(6-4) Photolyase in a 1:500 dilution. After extensive washing, the membrane was incubated with the appropriate secondary antibody in a 1:5000 dilution and then was conjugated to alkaline phosphatase. BCIP/NBT (Amresco) was used for immunodetection. (See FIG. 3)

Figure 4:
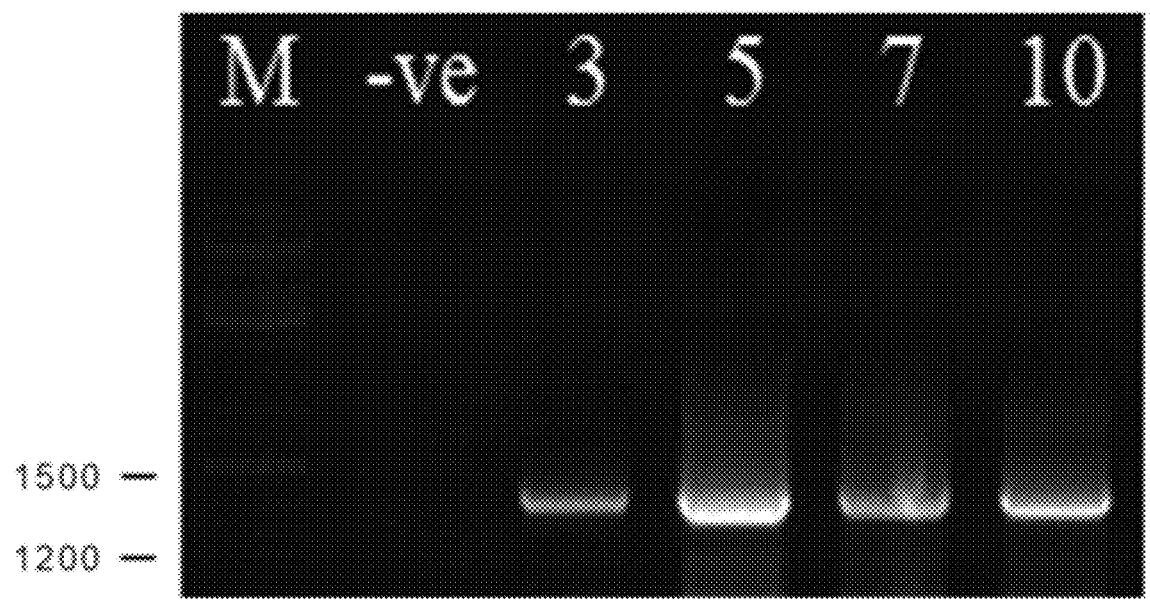
FIG. 4 shows RT-PCR results of CPD/6-4 photolyase-infiltrated *Nicotiana* leaves using custom primers, in an example for illustrating embodiments of the present invention.

For the detection of chimeric gene by real-time polymerase chain reaction (RT-PCR) an illustra RNAspin mini kit (GE healthcare) was used to extract, total RNA from the agroinfiltrated leaves. Oligonucleotides pair at the core region was designed to detect the presence of the phr and UVR3 gene at the core region; primers-forward: 5'-GCAC-GATTCAGCAAGCAAGG-3', and primers-reverse: 5'-CGGTACCTCTACCTATTTGAGTTTTG-3'. One step Real-Time PCR was carried out using SuperScript®III with Platinum® Taq DNA Polymerase. The reaction was resulted in the expected 1352 bp-fragment of the core region of the genes. (See FIG. 4)

To confirm the expression of the transgene after agroinfiltration, a direct ELISA protocol was carried out. ELISA-extraction buffer (2% PVP, 0.03 MNa$_2$SO$_3$) was used to extract total proteins. ELISA 96-well plates (Thermo Fisher Scientific) were coated with 250 µl antigen and total soluble protein, followed by overnight incubation at 4° C. Plates were washed three times with washing buffer the next day, three times, 5 minutes each. By adding 250 µl blocking buffer (PBS-Tween 20, 5% low-fat milk), the remaining protein-binding sites were blocked and incubated for 2.5 hrs at room temperature.

Figure 5:
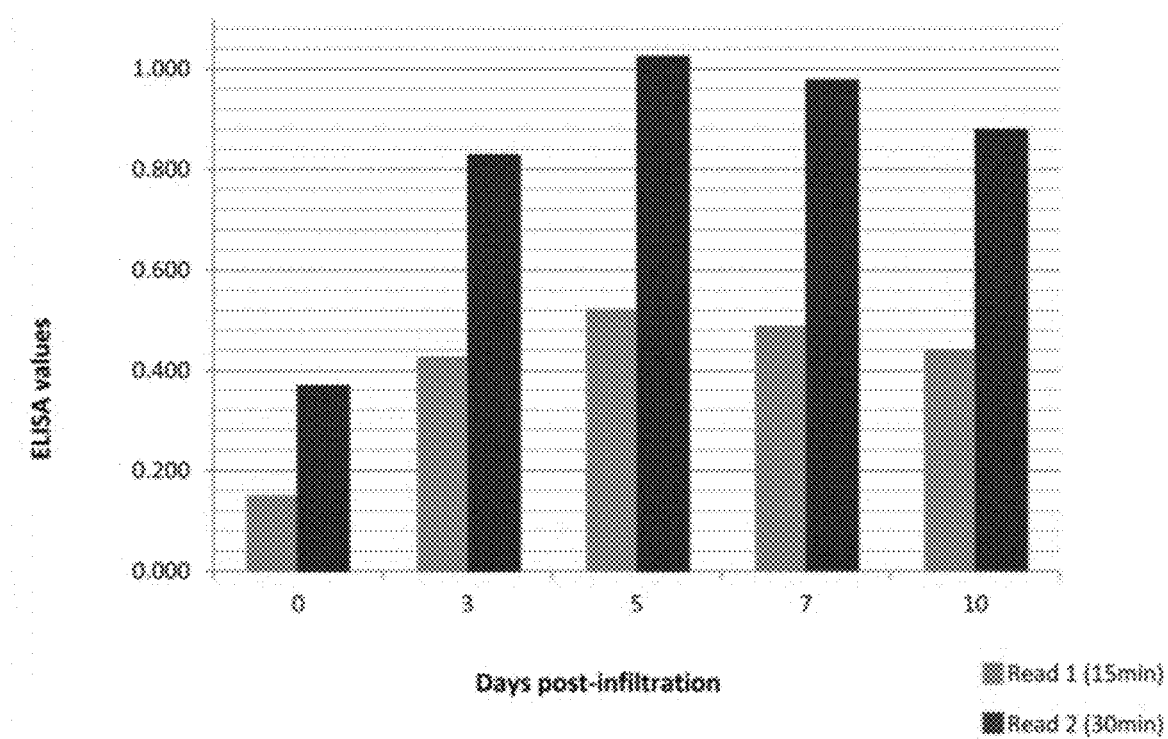
FIG. 5 illustrates ELISA reading values showing protein expression level over time intervals, post inoculation, in an example for illustrating embodiments of the present invention.

After washing with PBS and Tween 20, anti-CPD and anti-6-4PP antibodies were diluted by 1:1000 in a blocking buffer and 250 µl was added to each well. The plate was incubated in a humid chamber at 37.5° C. for 3.5 hrs. The plate was decanted and washed three times, 5 minutes each. 250 µl of substrate buffer (0.3 g (NaN$_3$), 96 ml diethanolamine, 600 ml H$_2$O) was added to the plate followed by incubation at room temperature until the color developed. With an automated ELISA reader (BIOBASE 2000), absorbencies were finally read at 630 nm wavelenght, 15 minutes each. ELISA values were expressed as the mean absorbance at wavelength ($\lambda$=640A°). Compared to negative control (C−), the S3, S5, S7 and S10 infiltrated samples showed positive result after 15 min and 30 min of read time. The highest expression level of PhR and UVR3 genes within *N. Benthamiana* leaves was obtained at the fifth day post-infiltration followed by descending in expression level at 7th and 10th days post-infiltration. (See FIG. 5)

The protein was purified by immobilised metal affinity chelating chromatography (IMAC). To immobilise the metal ions on Chelating Sepharose Fast Flow, a solution of 200 mM NiSO$_4$ (Sigma Aldrich) was passed through the column (GE Life Sciences). The column was washed with distilled water containing 0.02% azide to remove excess NiSO$_4$. The column was then equilibrated with 10 column volumes of buffer ANiS (50 mM Tris-HCl, pH 7.4, 50 mM NaCl, 100 mM Imidazole, 10 mM β-Mercaptoethanol, 0.02% (w/v) Azide) with the flow rate of 3 ml/min. The crude extract in buffer ANiS was applied to the column of Nickel Chelating Sepharose Fast Flow (column volume 10 ml) (GE Life Sciences). The column was washed with at least 10 column volumes of buffer ANiS, and was then switched to a linear gradient increasing the concentration of imidazole from 100 mM (buffer ANiS) to 500 mM of buffer BNiS (50 mM Tris-HCl, pH 7.4, 50 mM NaCl, 500 M Imidazole, 10 mM β-Mercaptoethanol, 0.02% (w/v) Azide.

To concentrate target protein, ultrafiltration was used. The protein solution was added to a stirred cell with a volume of either 10 ml or 50 ml (Amicon®, Millipore Sigma) and passed through an ultrafiltration cut disc regenerated cellulose membrane with a molecular weight cut off of 30 kDa (Ultracel®, Millipore Sigma). Using centrifugal filter devices (Microcon®, Millipore Sigma) according to the supplier's protocol, a concentration of small volumes of protein (300-600 µl) was achieved. To retain the targer protein, the exclusion limit of the membrane was selected.

Using UV/vis spectroscopy, the protein concentration was determined photometrically, which obeys the law of Beer-Lambert: A=$\epsilon\lambda$x·c·d, where A is the absorbance, $\epsilon$ the molar extinction coefficient at the specific wavelength $\lambda$ with units of M$^{-1}$ cm$^{-1}$, c is the concentration of the absorbing sample expressed in mol-L-1, and d the path length of the cuvette in cm.

The concentration of protein under denatured conditions was determined using the molar extinction coefficient for apo-photolyase $\epsilon$280 nm=106340 M$^{-1}$ cm$^{-1}$. The concentration of FAD synthetase in fusion with maltose binding protein was determined using the sum of the molar extinction coefficient $\epsilon$280 nm=28500 M$^{-1}$ cm$^{-1}$ for FAD synthetase and $\epsilon$280 nm=66350 M$^{-1}$ cm$^{-1}$ for maltose binding protein. The sequence for the maltose binding protein was provided from supplier Genscript, the molar extinction coefficient at 280 nm was calculated using the ProtParam tool from Expasy (http://www.expasy.ch).

Figure 6:
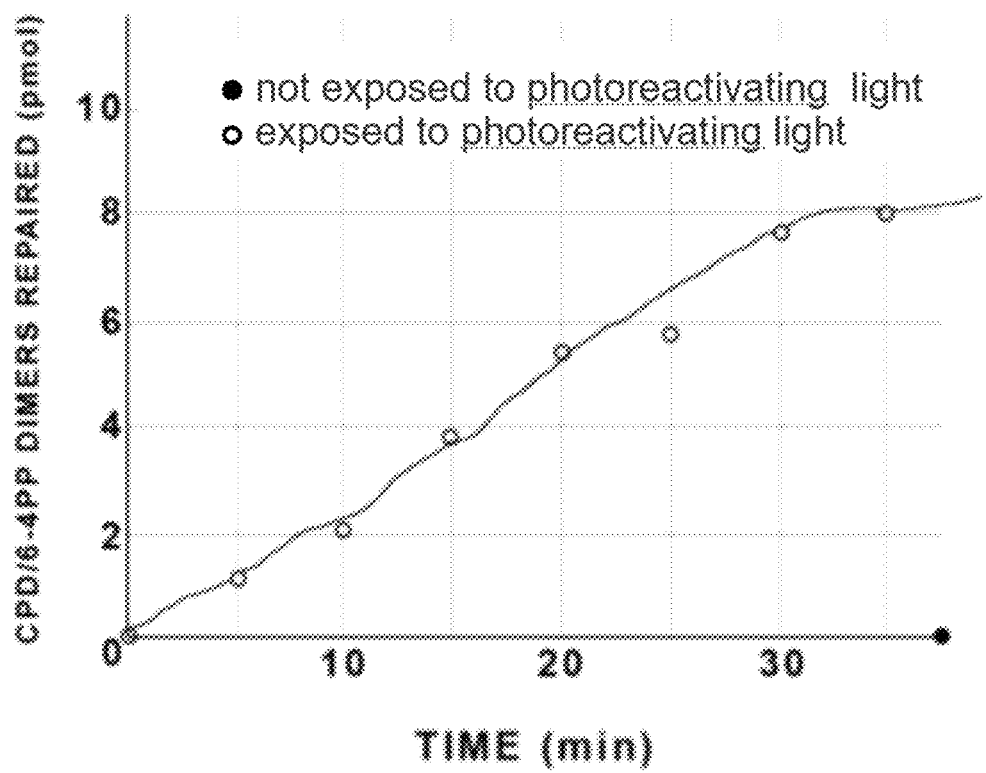
FIG. 6 shows specific activity of recombinant photolyase fusion enzyme, measured on supercoiled DNA plasmid, in an example for illustrating embodiments of the present invention.

Specific activity was detected whereas, 300 ng/µl of a 3,217 bp supercoiled plasmid, containing 25 potential CPD sites and 25 potential 6-4PP sites, was UV-irradiated with 100 J/m$^2$ of light at 254 nm, on ice. 1.5 µg of plasmid UV-irradiated with 0 J/m$^2$ and 100 J/m$^2$ were incubated with and without photolyase in buffer solution (12.5 mM Na$_2$HPO$_4$, 12.5 mM NaH$_2$PO$_4$, 1 mM EDTA, 0.1 mM DTT, and 100 mM NaCl) and 10 mM DTT (Thermo Fisher Scientific) in the dark for 5 minutes at room temperature in a 20 µl reaction volume. Reactions were then incubated under a near UV-visible light (75 W GE black-light, GE lighting) for one hour at room temperature. 250 ng of each sample of supercoiled plasmid was incubated with and without 15 units of our recombinant fusion enzyme, buffer solution (12.0 mM Na$_2$HPO$_4$, 12.5 mM NaH$_2$PO$_4$, 1 mM EDTA, 0.1 mM DTT, and 100 mM NaCl) at 37° C. for one hour. Reactions were resolved by electrophoresis on a 1% Trevigel 5000 gel (Trevigen) in 1×TAE buffer and 20 ng/ml ethidium bromide, and visualized under UV-light. As expected the recombinant fusion enzyme acts on UV-irradiated DNA only in the presence of photoreactivating light. The enzyme has no detectable endo- or exonuclease activity in the presence or absence of light and has no effect on transforming efficiency of nonirradiated DNA. We calculated a specific activity of 5×10$^6$ units/mg of enzyme and a turnover rate of 2.6 dimers/CPD-photolyase molecule/min and 1.8 Pyrimidine (6-4) pyrimidones/(6-4)photolyase respectively. One unit repaired 70% of 1 µg supercoiled plasmid irradiated with 100 J/m$_2$ UV-light in one hour at 37° C. during photoreactivation by 365 nm blue light at the rate of 2 mW/cm. The repair was measured as a loss in conversation of the supercoiled plasmid to relaxed, open circle form following treatment with the CPD/6-4PP specific fusion photolyase. (See FIG. 6)

Additionally, the recombinant fusion enzyme has demonstrated to be very stable both at 4° C. and at 22° by a comparative stability assay. In order to correlate with the recombinant photolyase fusion enzyme solution, a fraction containing native CPD Photolyase and 6-4 Photolyase enzymatic activity were adjusted to a concentration of 20 ng/µl with bovine serum albumin (BSA, Thermo Fisher Scientific) and divided in several tubes. Half of the tubes were stored at 4° C. and the remaining tubes were stored at a temperature of 22° C. The same procedure was applied to the recombinant photolyase fusion enzyme solution.

Figure 7:
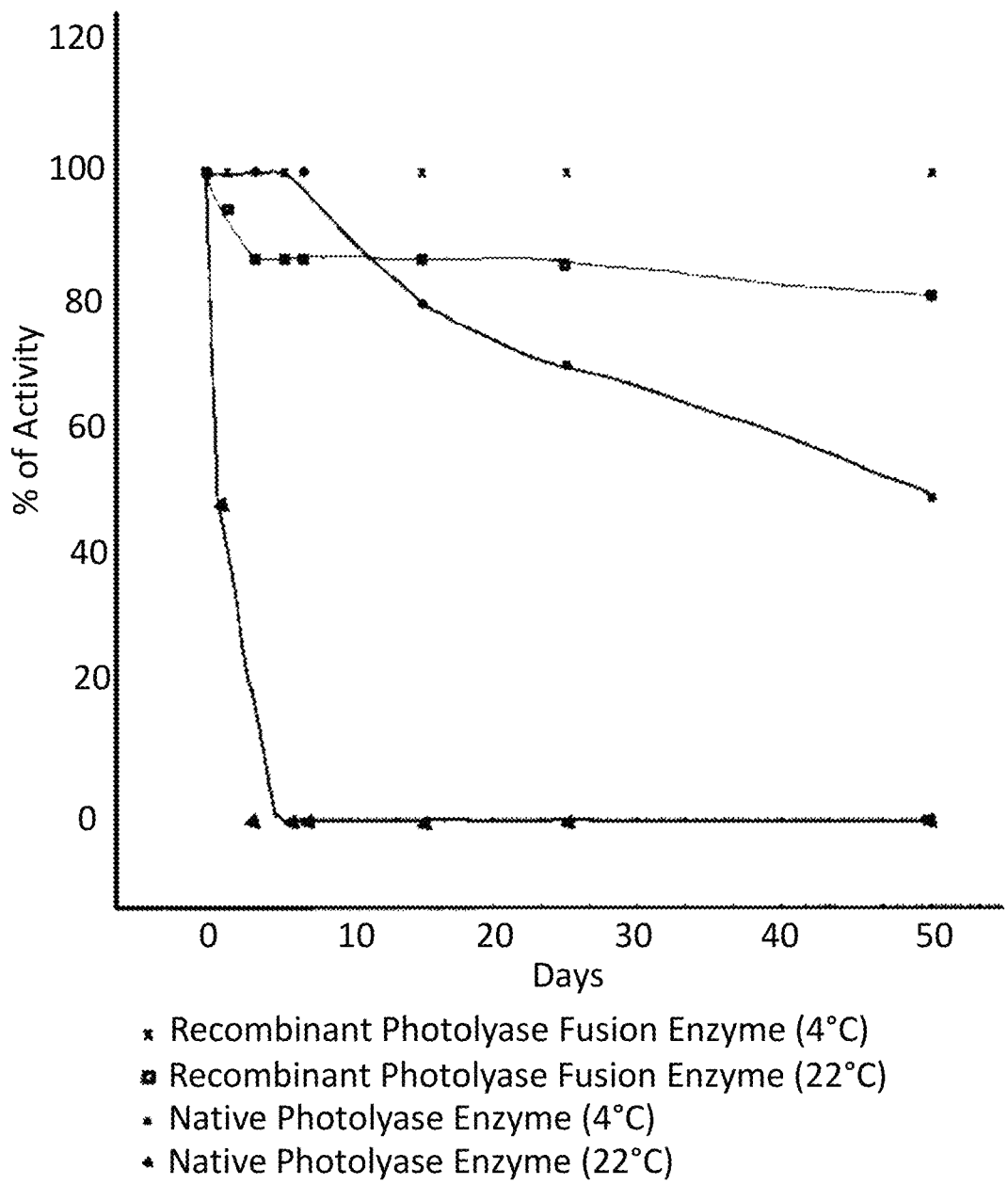
FIG. 7 shows a comparative stability assay of recombinant photolyase fusion enzyme versus native photolyase, in an example for illustrating embodiments of the present invention.

Both native CPD photolyase, (6-4) photolyase and the recombinant photolyase fusion enzyme preparations, stored at respective temperatures of 4° C. and 22° C., were scanned for their enzymatic activity, over a course of 2 years storage period. The percentage of relaxed irradiated plasmid was quantified by electrophoresis in agarose gel (Thermo Fisher Scientific). Both native CPD photolyase and (6-4) photolyase activity decreased over the first days of storage at room temperature. On the other hand, the recombinant photolyase fusion enzyme kept the percentage of activity closer to 100% until the end of the storage period. These values were kept between 75-85% at 4° C., for a period of 24 months. (see FIG. 7)

The recombinant photolyase fusion enzyme can be directed through the stratum corneum, into cells where it can exert its beneficial effect on DNA distorted by damage such as that from ultraviolet irradiation or other deleterious agents that cause distortions within both single and double-stranded DNA. The fusion of the skin penetrating peptide moiety (Keratin Binding Peptide, KBP) with the recombinant photolyase fusion enzyme allowed us to directly deliver protein into human skin keratinocytes (Normal Human Epidermal Keratinocytes, NHEK, PromoCell). Keratinocytes are useful for proof-of-principle studies because they represent the precursor cells that can develop into basal and squamous cell carcinomas, the most frequently occurring human skin cancers caused by chronic exposure to sunlight. Optimal conditions (incubation of cells with protein in PBS buffer for 30 minutes at room temperature) for protein delivery into human skin cells was established and verified via immunocytochemistry and western blot analysis.

As a preliminary, a cytotoxicity test was performed to determine if the used doses were tolerable and usable in the efficacy test on cells. The products were dissolved in the culture medium in the conditions chosen after a solubility test. Cells were cultured with the recombinant photolyase fusion enzyme for 24 hours minimum. During the last 3 hours, WST1 reagent (Roche) was added to the culture medium. The reagent contains tetrazolium salts, a violet indicator, which is cleaved into formazan, a yellow indicator, by metabolically active cells. The level of yellowing is proportional to the number of living cells. Absorbance was measured at 450 nm. Furthermore, the cells were observed by microscopy to validate cell shape. The final concentration of treatment was set at a maximum of 15 µg/ml.

Figure 8:
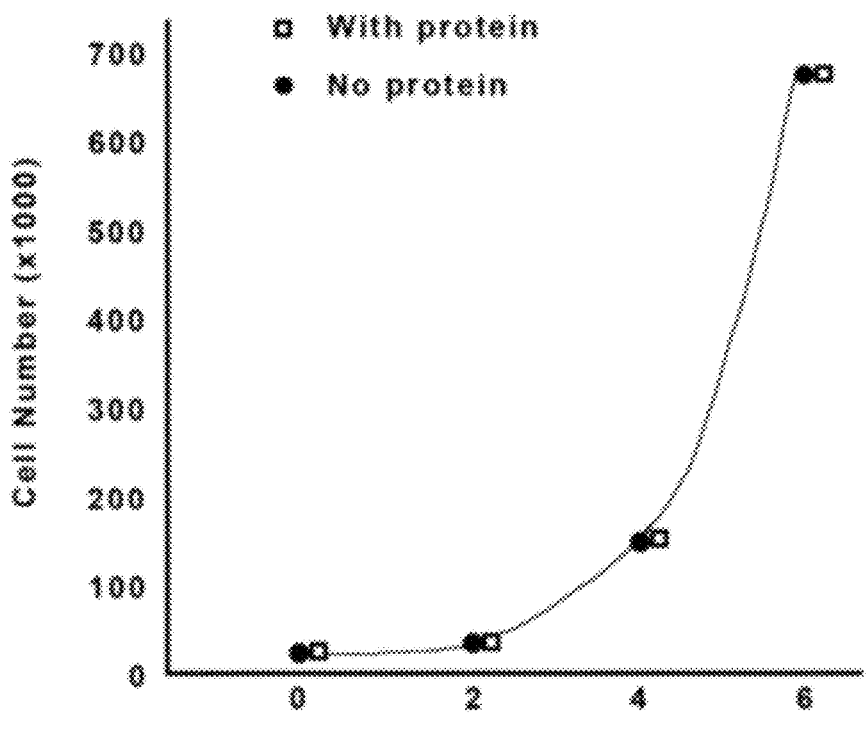
FIG. 8 shows the cytotoxic effect of the recombinant photolyase fusion enzyme on NHEK cell growth, in an example for illustrating embodiments of the present invention.

The effect of the recombinant photolyase fusion enzyme on NHEK cell growth was determined in assess the potential cytotoxic or cytostatic effects mediated by this protein. Exposure to doses of the recombinant photolyase fusion enzyme that result in protection from UV light-induced DNA damage and cytotoxicity did not result in any measurable effects on cell growth or viability. We have concluded that at the doses tested, the recombinant photolyase fusion enzyme is non-toxic. (see FIG. 8)

To examine whether the recombinant photolyase fusion enzyme reduces celllar DNA damage levels by UV exposure, four types of studies were conducted.

Figure 9:
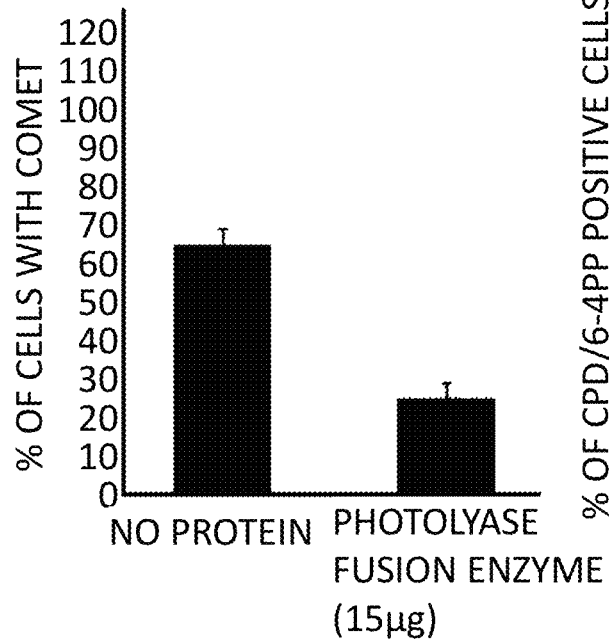
FIG. 9 shows a reduction of DNA damage-induced comets, in an example for illustrating embodiments of the present invention.
Figure 10:
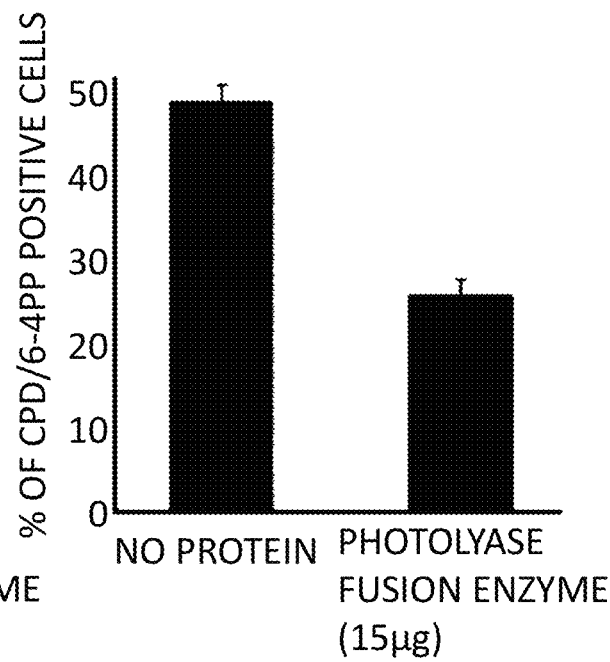
FIG. 10 shows a number of CPD/6-4PP positive cells, in an example for illustrating embodiments of the present invention.

The first study is based on a custom comet assay, which are based on the principle that nuclear DNA containing unpaired damages are fragmented following UV irradiation and alkali exposure causing broken DNA fragments to migrate out of the nucleus to form a "comet" following electrophoresis of the cell/DNA slide preparations were performed. Such comets are visualized and quantified via microscopic analysis of stained DNA. Thus, such assay determines the overall level of cellular DNA damage level. UV-irradiated NHEK exposed to non-toxic doses of recombinant photolyase fusion enzyme demonstrated a significant reduction of DNA damage-induced comets, indicating that it can initiate the repair of UV damage in vivo. To directly assess the levels of CPD and (6-4)PP photopdructs in human NHEK, following to UV exposure, this observation has been verified using a direct immunocytochemical assay employing a monoclonal antibodies against CPDs and (6-4) PPs. Our recombinant photolyase fusion enzyme demonstrated a reduction of the overall CPD and 6-4pp levels in cells by about 45-50%, thus capable of initiating the repair and elimination of highly cytotoxic DNA damage caused by UV light in human keratinocytes. (see FIGS. 9 and 10)

Figure 11:
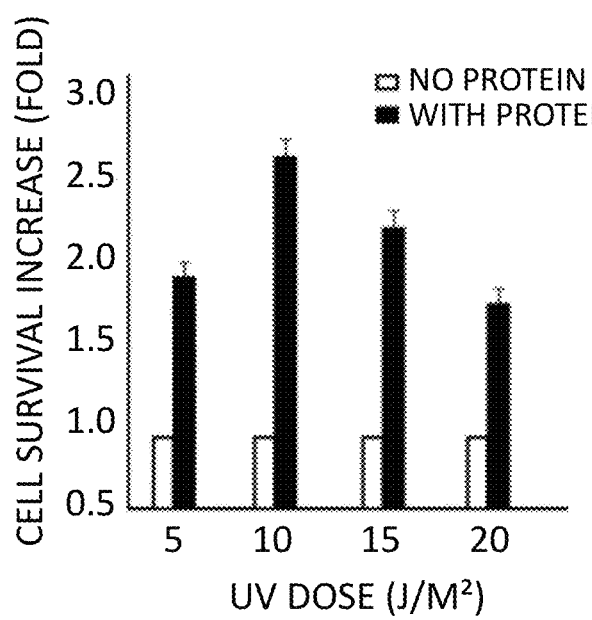
FIG. 11 shows an increase in cell survival (NHEK), in an example for illustrating embodiments of the present invention.
Figure 12:
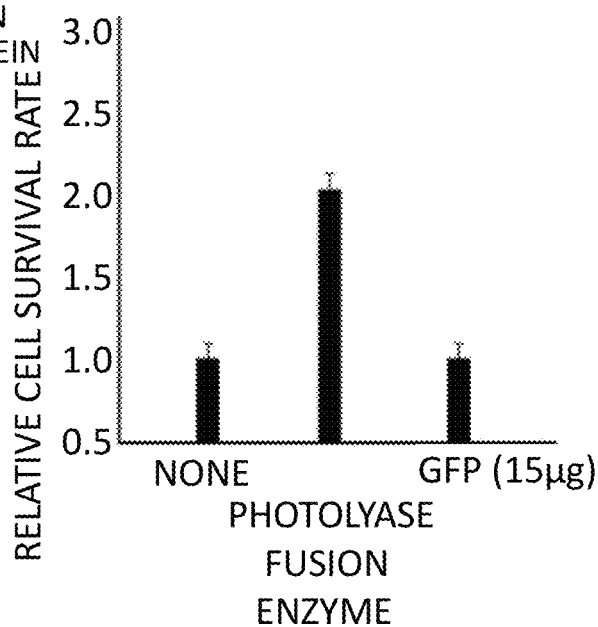
FIG. 12 shows relative cell survival rate (NHEK), in an example for illustrating embodiments of the present invention.

To further examine whether our recombinant photolyase fusion enzyme increases cell survival after UV exposure, a second study was conducted, utilizing a colony formation assay. This assay was used to conduct multiple experiments under various UV exposure conditions. Our results demonstrate that our recombinant photolyase fusion enzyme increases NHEK survival following UV exposure, that the average increase in cell survival is about 2.5-fold, and that the increase in cell survival conferred by our recombinant photolyase fusion enzyme is specific for this DNA repair enzyme, since incubation of comparison protein green fluorescent protein (GFP, Thermo Fisher Scientific) following UV exposure was without effect. (see FIGS. 11 and 12)

Figure 13:
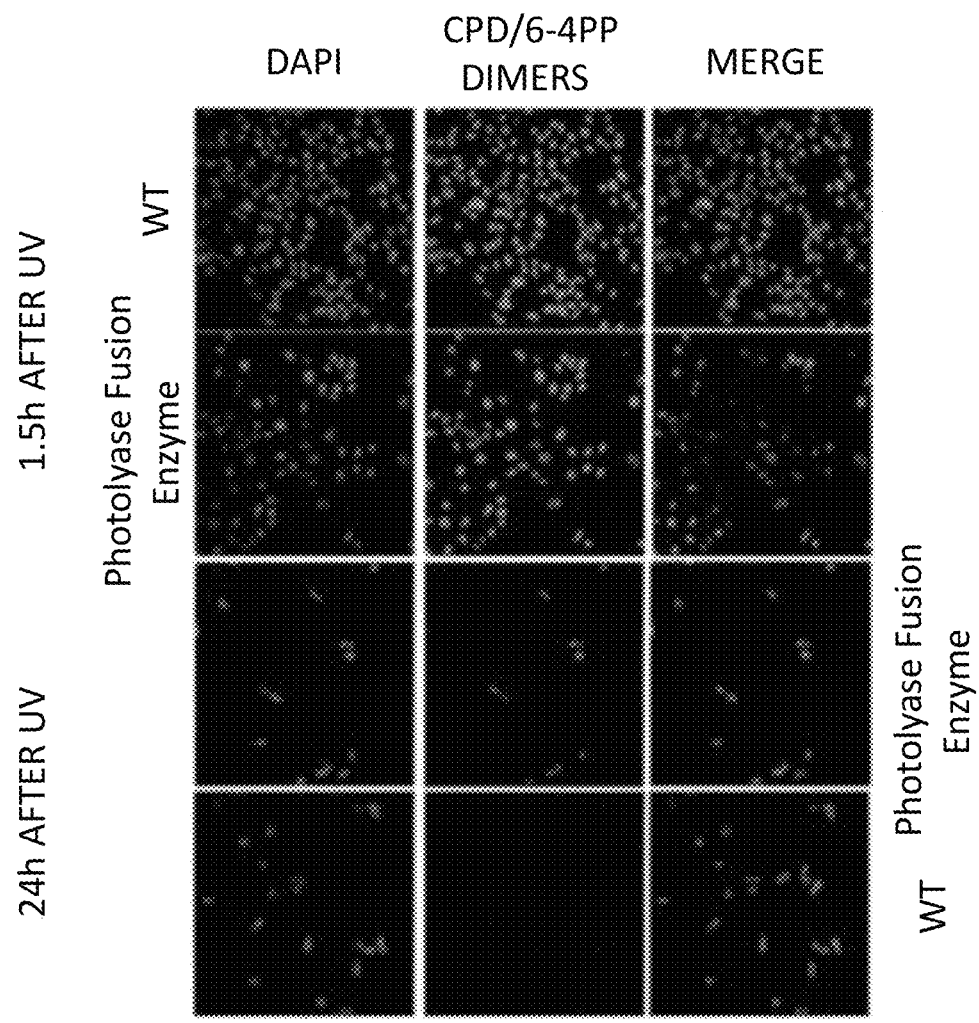
FIG. 13 shows a quantification of CPD/6-4PP dimers on NHEK using fluorescence microscopy, in an example for illustrating embodiments of the present invention.

A third study was carried out on NHEK, n=3 minimum, whereas; the NHEK were seeded in a 96-well plate in cell culture medium and incubated 24 h at 37° C., 5% CO2. The cells exposed to UV were treated with the recombinant photolyase fusion enzyme. Then the cells were washed and fixed in Formalin. After permeabilization, the cells were incubated with antibodies; anti-CPD and anti-6-4PP and revealed with a secondary antibody linked to Alexa488 (Alexa Fluor® 488, Thermo Fisher Scientific). Finally, the cell nuclei were labeled with DAPI (4',6-Diamidino-2-Phenylindole, Dihydrochloride, Thermo Fisher Scientific). The labeled proteins will be observed and quantified by automated fluorescence microscopy (Lumascope 720 Automated Fluorescence Microscope, Etaluma). The measured fluorescence was analyzed by Image analysis (Image J) and the quantity of positive cells for CPDs and 6-4PPs were quantified. A significant reduction in CPDs and 6-44PPs was measured. (see FIG. 13)

Figure 14:
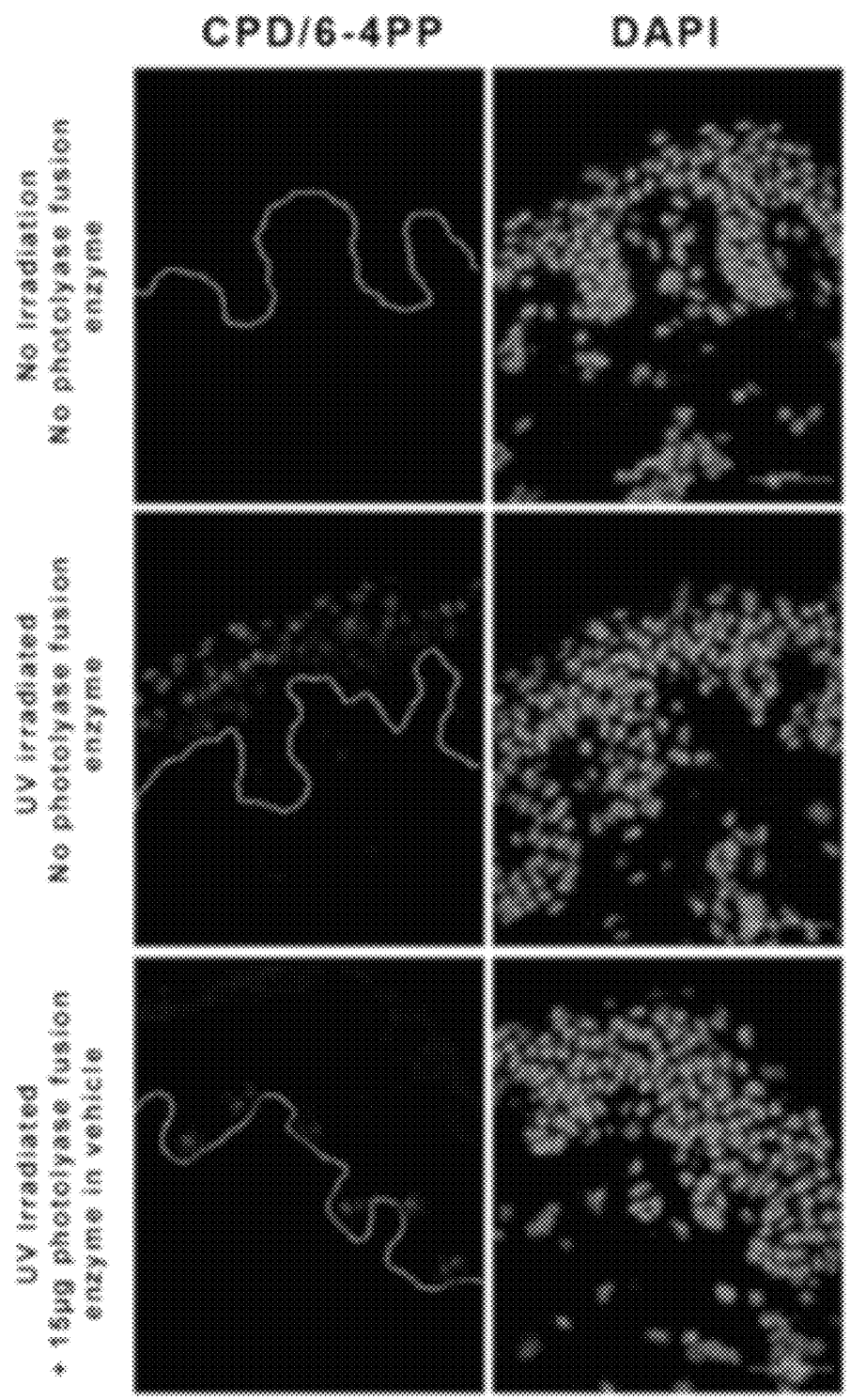
FIG. 14 shows a quantification of CPD/6-4PP dimers on Human skin explants using fluorescence microscopy, in an example for illustrating embodiments of the present invention.

The fourth study was carried on human skin explants (NativeSkin®, Genoskin), a full-thickness skin biopsy embedded in a solid and nourishing matrix while its epidermal surface is left in contact with air. The skin biopsy is firmly embedded in the matrix that prevents any lateral diffusion of topically applied formulations. The experiment was carried out in triplicate n=3 with a hydrogel used as a vehicle. After treatment, skin explants were fixed with formalin, embedded in paraffin and sectioned. CPD (Cyclobutane Pyrimidine Dimers) and 6-4PP (pyrimidine dimers: 6,4 photoproduct) were labelled by immunofluorescence and observed by fluorescence microscopy (DM5000B, Leica Microsystems). The measured fluorescence was analyzed by Image analysis (Image J) and the quantity of positive cells for Pyrimidine dimers was quantified. A significant reduction in CPDs and 6-4PPs was measured. (see FIG. 14)

Based on the data provided herein, we have concluded within the context of a human skin keratinocyte cell culture system and a human skin explant system, which are appropriate and accepted models for UV photocarcinogenesis studies, that our recombinant photolyase fusion enzyme penetrates cells and localizes to the nucleus upon exposure of cells to purified protein; that it initiates the repair of UV radiation-induced cytotoxic, mutagenic and carcinogenic DNA damage; and that it increases the survival of UV-damaged cells at non-toxic doses. The degree of protection contributed by our recombinant photolyase fusion enzyme is biologically significant as even small increased in the overall DNA repair capacity of cells can translate into a major, additional protective effect against photoaging and photocarcinogenesis, especially in the context of UV exposure that otherwise would result in DNA damage, characterized by distortion of both single-stranded and double-stranded DNA.

Furthermore we demonstrated that the expression of a stable and bioavailable biosynthetic recombinant photolyase fusion enzyme via agroinfiltration into *N. benthamiana* was succesfully achieved. Additionally, the expression system used for this recombinant enzyme is able to produce huge amounts of recombinant product at a low-cost, which is primordial in terms of commercialization; and that this production level can still be increased if the process is optimized at industrial levels, simply by sufficient upscaling of growing plants without re-engineering processes.

The afore-described method includes the preparation and purification method for the novel recombinant photolyase fusion enzyme; as well as its utilization as part of a cosmetic and/or pharmaceutical formula intended to repair DNA lesions and/or cell abnormalities produced by UV light exposure and/or the treatment and prevention and prophylaxis of premature photoaging and photocarcinogenesis, actinic keratosis, xeroderma pigmentosum and non-melanoma skin cancer.

The invention claimed is:

1. A composition comprising a recombinant enzyme that comprises a fusion of a cyclobutane pyrimidine dimer photolyase corresponding to an amino acid encoding sequence of SEQ ID NO 1,
 a pyrimidine(6-4)pyrimidone photolyase corresponding to an amino acid encoding sequence of SEQ ID NO 2, and
 a skin penetrating peptide.

2. The composition of claim 1, wherein said skin penetrating peptide is encoded by the DNA sequence of SEQ ID NO 3.

3. The composition of claim 1, wherein said recombinant enzyme is a deazaflavin photolyase.

4. The composition of claim 1, wherein said recombinant enzyme comprises one or more tag peptides to facilitate purification of the recombinant enzyme.

5. The composition of claim 1, further comprising a carrier and/or an excipient to facilitate uptake of the composition in or on the body.

6. The composition of claim 5, wherein said carrier and/or said excipient comprises an encapsulating material for at least temporarily encapsulating at least said fusion.

7. The composition of claim 6, wherein said carrier and/or said excipient further comprises a liposome and/or thermo-responsive polyglycerol particles.

8. The composition of claim 1, further comprising a solubilizer, a skin permeation enhancer, a preservative, a moisturizer, a gelling agent, a buffering agent, a surfactant, an emulsifier, an emollient, a thickening agent, a stabilizer, a humectant, a dispersing agent and/or any combination thereof.

9. A nucleic acid molecule comprising a first fragment corresponding to SEQ ID NO: 1, coding for cyclobutane pyrimidine dimer photolyase, a second fragment corresponding to SEQ ID NO: 2, coding for a pyrimidine(6-4) pyrimidone photolyase and a third fragment that encodes a skin penetrating peptide.

10. The nucleic acid molecule of claim 9, wherein the third fragment has at least a 85% sequence identity to SEQ ID NO: 3.

11. The nucleic acid molecule of claim 9, further comprising a His-tag for facilitating purification.

12. A nucleic acid vector comprising the nucleic acid molecule of claim 9 and transcription and translation control sequences effective to initiate transcription and subsequent protein synthesis in a host cell.

13. The nucleic acid vector of claim 12, wherein said nucleic acid vector has at least a 85% sequence identity to SEQ ID NO:4.

14. The nucleic acid vector of claim 12, wherein said host cell is a *Nicotiana Benthamiana* cell.

15. A transgenic *Nicotiana Benthamiana* plant or the seed thereof, the plant or seed comprising the nucleic acid molecule according to claim 9.

* * * * *

SEQUENCE LISTING

```
<160> NUMBER OF SEQ ID NOS: 8

<210> SEQ ID NO 1
<211> LENGTH: 1260
<212> TYPE: DNA
<213> ORGANISM: Artificial
<220> FEATURE:
<223> OTHER INFORMATION: cpd photolyase from thermus thermophilus, codon
      optimized for nicotiana benthamiana species

<400> SEQUENCE: 1
atgggcccct tgctcgtgtg gcacaggggc gatttgagat tacatgacca tcccgcattg      60
ttggaggccc tcgcaagggg accggtggta gggttagttg ttctcgaccc aaataacctt     120
aagactacac cgaggagaag agcttggttc ctcgagaatg taagggccct gcgagaggct     180
taccgtgcaa ggggcggtgc tctctgggtc ttggagggct tgccctggga aaaagtgccc     240
gaagctgctc gaaggttgaa ggctaaagcc gtctatgcat taactagcca cacgccttat     300
gggaggtata gagatggccg agtaagagaa gcacttcccg tgcctctcca cttattgcca     360
gcccctcacc tgctgccgcc agatcttccg agggcatacc gagtctacac gccgttcagt     420
aggttgtacc gtggcgcagc ccctccatta ccaccacccg aggcactccc aaagggtcca     480 gaagagggg aaataccctcg tgaggaccca gggctcccgc tccctgagcc tggagaagaa     540
gctgctttag ccggccttcg tgcctttctg gaagcaaaat tgccacgtta cgccgaggaa     600
cgagatcgtc ttgatggcga aggtggctct cgtctgtctc cgtattttgc tcttggggta     660
ttatccccac gtctggcagc ctgggaagca gagaggcgag ggggagaggg cgcaaggaaa     720
tgggtcgctg aattattatg gcgagacttt tcatatcacc tcctttatca ctttccttgg     780
atggccgagc gacctcttga tcctcgtttt caggccttcc cgtggcagga ggatgaagca     840 cttttttcagg cttggtacga gggaaaaact ggtgtgccat tggttgacgc cgctatgagg     900
gaattgcatg caaccggatt cctgagtaat cgtgcacgaa tgaacgcagc tcaattcgca     960
gtcaaacatt tacttcttcc atggaaaagg tgtgaagaag cctttcgaca cttgctcctg    1020
gacggcgacc gtgcagtcaa cctgcaggga tggcaatggg caggcggcct ggggtggat    1080 gctgctcctt actttagggt gtttaatccg gtcctgcagg gggagagaca cgacccgaa    1140 ggccgttggt taaaacgttg ggcacctgag taccctagct atgcccccaa ggacccagta    1200
gtggacttag aggaggcccg tcgacgttac ctcaggctcg cccgagattt agcaaggggc    1260

<210> SEQ ID NO 2
<211> LENGTH: 1521
<212> TYPE: DNA
<213> ORGANISM: Artificial
<220> FEATURE:
<223> OTHER INFORMATION: (6-4) photolyase from Arabidopsis thaliana,
      codon optimized for Nicotiana benthamiana species

<400> SEQUENCE: 2
```

```
atgagtcaat tggtattgat tctcggtgat cagttaagcc cctcaatagc tgcactcgac    60
ggggtcgata agaaacagga cacgatcgtt ctctgtgagg tgatggctga ggcctcctac   120
gttggccatc acaaaaaaaa aatagcattt atttttttccg caatgagaca tttcgcagag   180
gaattgagag gtgagggggta ccgtgtaaga tatactcgta tagacgatgc agataacgct   240
ggtagcttta ctggtgaagt gaagcgagca atagacgatc tgactccgtc aagaatttgc   300
gtcactgaac caggtgagtg gcgtgtacga agcgagatgg atggcttcgc cggtgccttt   360
ggaatacagg tcgatatacg tagcgaccgt agatttttga gttcccacgg ggagttcaga   420
aactgggcag ctggccgaaa gtctcttacc atggaatatt tctatcgaga atgagaagg    480
aagacggggt tgctcatgaa cggggagcag cccgttggtg ggcgttggaa tttcgacgca   540
gagaaccgac aaccagcccg accagatctc ttaaggccga acacccccgt ctttgctccg   600
gataagatca caaggaagt tatcgatacc gtggagcgtt tgttcccccga taacttcggg   660
aaattggaga actttggatt tgcagtaact agaacagatg ccgagcgtgc tttatctgca   720
ttcattgatg atttttctctg caatttcgga gcaacgcaag atgctatgtt acaagatgac   780
ccgaatctca atcactcttt gctcagcttt tatatcaact gtggtctcct tgatgcatta   840
gatgtctgca aggcagctga aagagcctac catgagggag gtgcaccatt aaatgccgtt   900
gaaggtttca tcagacaaat tataggatgg cgagaataca tgaggggtat ctattggtta   960
gctggaccgg attatgtgga ttccaacttc tttgagaatg atagatcact tccagttttt  1020
tattggaccg gaaaaacgca tatgaactgt atggctaagg tgattactga aacaatcgag  1080
aacgcatatg cccatcacat acaaagactg atgatcacag gaatttttcgc cttgttggct  1140
ggtattgacc caaaagccgt gcatagatgg tatctcgagg tttatgccga tgcctatgag  1200
tgggtcgagc tgccaaatgt aattggtatg tcacagtttg ctgacggggg cttcctcggc  1260
acaaaacctt acgccgctag tggtaactat ataaacagga tgtctgacta ttgcgacacc  1320
tgtagatacg acccgaagga gcgtttagga gataatgctt gccccttaa tgcccttat    1380
tgggactttc tcgcaaggaa ccgagagaag ctgaaatcca atcatagact ggctcaaccg  1440
tacgccacct gggcaaggat gagcgaggac gttagacacg acctcagggc caaggcagca  1500
gcattcctca ggaaacttga c                                             1521

<210> SEQ ID NO 3
<211> LENGTH: 39
<212> TYPE: DNA
<213> ORGANISM: Artificial
<220> FEATURE:
<223> OTHER INFORMATION: synthesized

<400> SEQUENCE: 3
gctgcttgtt cttcttctcc atctaagcat tgtggagga                            39

<210> SEQ ID NO 4
<211> LENGTH: 6118
<212> TYPE: DNA
<213> ORGANISM: Artificial
<220> FEATURE:
<223> OTHER INFORMATION: synthesized vector

<400> SEQUENCE: 4
caactttgta tagaaaagtt gtgagacttt tcaacaaagg gtaatatccg gaaacctcct     60
cggattccat tgcccagcta tctgtcactt tattgtgaag atagtggaaa aggaaggtgg   120
ctcctacaaa tgccatcatt gcgataaagg aaaggccatc gttgaagatg cctctgccga   180
```

```
cagtggtccc aaagatggac ccccacccac gaggagcatc gtggaaaaag aagacgttcc    240
aaccacgtct tcaaagcaag tggattgatg tgatatctcc actgacgtaa gggatgacgc    300
acaatcccac tatccttcgc aagacccttc ctctatataa ggaagttcat ttcatttgga    360
gagaacacaa gtttgtacaa aaaagcaggc tgccaccatg catcaccacc atcaccacga    420
gagagctata cagggtaatg atgcccgtga acaagctaat agtgaaaggt gggacggagg    480
aagtgggggt acgacaagtc cattcaagct cccagacgaa agtcctagct ggaccgagtg    540
gcgattacac aatgacgaga ctaattccaa ccaggacaat ccccttggat ttaaggaaag    600
ttggggattc gggaaagttg ttttcaagcg ttatcttaga tacgacagaa cagaagcttc    660
cttgcataga gttctcgggt cctggacagg ggacagcgtt aattacgcag catccaggtt    720
cttcggattc gatcagatag gctgtactta cagcataaga ttcagagggg tgtccattac    780
ggtgagtgga ggctccagga ctctccaaca tttatgcgag atggctataa ggagcaagca    840
ggaattgtta caactggccc cgattgaagt cgagagcaat gtctcaagag gttgtcccga    900
aggcactgaa acgtttgaaa aggagtccga agcctgttca tcctctccta gcaagcactg    960
tgggatgggc cccttgctcg tgtggcacag gggcgatttg agattacatg accatcccgc   1020
attgttggag gccctcgcaa ggggaccggt ggtagggtta gttgttctcg acccaaataa   1080
ccttaagact acaccgagga gaagagcttg gttcctcgag aatgtaaggg ccctgcgaga   1140
ggcttaccgt gcaaggggcg tgctctctg gtcttggag ggcttgccct gggaaaaagt     1200
gcccgaagct gctcgaaggt tgaaggctaa agccgtctat gcattaacta gccacacgcc   1260
ttatgggagg tatagagatg gccgagtaag agaagcactt cccgtgcctc tccacttatt   1320
gccagcccct cacctgctgc cgccagatct tccgagggca taccgagtct acacgccgtt   1380
cagtaggttg taccgtggcg cagcccctcc attaccacca cccgaggcac tcccaaaggg   1440
tccagaagag ggggaaatac ctcgtgagga cccaggctc ccgctccctg agcctggaga    1500
agaagctgct ttagccggcc ttcgtgcctt tctggaagca aaattgccac gttacgccga   1560
ggaacgagat cgtcttgatg gcgaaggtgg ctctcgtctg tctccgtatt ttgctcttgg   1620
ggtattatcc ccacgtctgg cagcctggga agcagagagg cgaggggag agggcgcaag    1680 gaaatgggtc gctgaattat tatggcgaga cttttcatat cacctccttt atcactttcc   1740
ttggatggcc gagcgacctc ttgatcctcg ttttcaggcc ttcccgtggc aggaggatga   1800 agcactttt caggcttggt acgagggaaa aactggtgtg ccattggttg acgccgctat    1860
gagggaattg catgcaaccg gattcctgag taatcgtgca cgaatgaacg cagctcaatt   1920
cgcagtcaaa catttacttc ttccatggaa aaggtgtgaa gaagcctttc gacacttgct   1980 cctgacggc gaccgtgcag tcaacctgca gggatgcaa tgggcaggcg gcctgggggt     2040
ggatgctgct ccttacttta gggtgtttaa tccggtcctg caggggagga gacacgaccc   2100
ggaaggccgt tggttaaaac gttgggcacc tgagtaccct agctatgccc caaggaccc    2160 agtagtggac ttagaggagg cccgtcgacg ttacctcagg ctcgcccgag atttagcaag   2220
gggcggagga ggagggtccg ggggcggcg gtcaggaggg ggaggttcaa tgagtcaatt    2280
ggtattgatt ctcggtgatc agttaagccc ctcaatagct gcactcgacg gggtcgataa   2340
gaaacaggac acgatcgttc tctgtgaggt gatggctgag gcctcctacg ttggccatca   2400
caaaaaaaaa atagcattta ttttttccgc aatgagacat ttcgcagagg aattgagagg   2460
tgaggggtac cgtgtaagat atactcgtat agacgatgca gataacgctg gtagctttac   2520
```

```
tggtgaagtg aagcgagcaa tagacgatct gactccgtca agaatttgcg tcactgaacc   2580
aggtgagtgg cgtgtacgaa gcgagatgga tggcttcgcc ggtgcctttg aatacaggt    2640 cgatatacgt agcgaccgta gattttgag ttcccacggg gagttcagaa actgggcagc    2700
tggccgaaag tctcttacca tggaatattt ctatcgagaa atgagaagga gacggggtt    2760 gctcatgaac ggggagcagc ccgttggtgg gcgttggaat tcgacgcag agaaccgaca    2820 accagcccga ccagatctct taaggccgaa acaccccgtc tttgctccgg ataagatcac   2880
aaaggaagtt atcgataccg tggagcgttt gttccccgat aacttcggga aattggagaa   2940
ctttggattt gcagtaacta gaacagatgc cgagcgtgct ttatctgcat tcattgatga   3000
ttttctctgc aatttcggag caacgcaaga tgctatgtta caagatgacc cgaatctcaa   3060
tcactctttg ctcagctttt atatcaactg tggtctcctt gatgcattag atgtctgcaa   3120
ggcagctgaa agagcctacc atgagggagg tgcaccatta aatgccgttg aaggtttcat   3180
cagacaaatt ataggatggc gagaatacat gaggggtatc tattggttag ctggaccgga   3240
ttatgtggat tccaacttct tgagaatga tagatcactt ccagttttt attggaccgg     3300 aaaaacgcat atgaactgta tggctaaggt gattactgaa acaatcgaga acgcatatgc   3360
ccatcacata caaagactga tgatcacagg aaatttcgcc ttgttggctg gtattgaccc   3420
aaaagccgtg catagatggt atctcgaggt ttatgccgat gcctatgagt gggtcgagct   3480
gccaaatgta attggtatgt cacagttttgc tgacgggggc ttcctcggca caaaaccta    3540 cgccgctagt ggtaactata taaacaggat gtctgactat tgcgacacct gtagatacga   3600
cccgaaggag cgtttaggag ataatgcttg cccctttaat gccctttatt gggactttct   3660
cgcaaggaac cgagagaagc tgaaatccaa tcatagactg gctcaaccgt acgccacctg   3720
ggcaaggatg agcgaggacg ttagacacga cctcagggcc aaggcagcag cattcctcag   3780
gaaacttgac tagacccagc tttcttgtac aaagtggtag ctcgaatttc cccgatcgtt   3840
caaacatttg gcaataaagt ttcttaagat tgaatcctgt tgccggtctt gcgatgatta   3900
tcatataatt tctgttgaat tacgttaagc atgtaataat taacatgtaa tgcatgacgt   3960
tatttatgag atgggttttt atgattagag tcccgcaatt atacatttaa tacgcgatag   4020
aaaacaaaat atagcgcgca aactaggata aattatcgcg cgcggtgtca tctatgttac   4080
tagatcggga aggccgcggc gctcttccgc ttcctcgctc actgactcgc tgcgctcggt   4140
cgttcggctg cggcgagcgg tatcagctca ctcaaaggcg gtaatacggt tatccacaga   4200
atcaggggat aacgcaggaa agaacatgtg agcaaaaggc cagcaaaagg ccaggaaccg   4260
taaaaaggcc gcgttgctgg cgttttccca taggctccgc cccctgacg agcatcacaa    4320 aaatcgacgc tcaagtcaga ggtggcgaaa cccgacagga ctataaagat accaggcgtt   4380
tccccctgga agctccctcg tgcgctctcc tgttccgacc ctgccgctta ccggatacct   4440
gtccgccttt ctcccttcgg gaagcgtggc gctttctcat agctcacgct gtaggtatct   4500
cagttcggtg taggtcgttc gctccaagct gggctgtgtg cacgaacccc ccgttcagcc   4560
cgaccgctgc gccttatccg gtaactatcg tcttgagtcc aacccggtaa gacacgactt   4620
atcgccactg gcagcagcca ctggtaacag gattagcaga gcgaggtatg taggcggtgc   4680
tacagagttc ttgaagtggt ggcctaacta cggctacact agaagaacag tatttggtat   4740
ctgcgctctg ctgaagccag ttaccttcgg aaaaagagtt ggtagctctt gatccggcaa   4800 acaaccacc gctggtagcg gtggtttttt tgtttgcaag cagcagatta cgcgcagaaa     4860
aaaaggatct caagaagatc ctttgatctt ttctacgggg tctgacgctc agtggaacga   4920
```

-continued

```
aaactcacgt taagggattt tggtcatgag attatcaaaa aggatcttca cctagatcct    4980
tttaaattaa aaatgaagtt ttaaatcaat ctaaagtata tatgagtaaa cttggtctga    5040
cagttaccaa tgcttaatca gtgaggcacc tatctcagcg atctgtctat ttcgttcatc    5100
catagttgcc tgactccccg tcgtgtagat aactacgata cgggagggct taccatctgg    5160
ccccagtgct gcaatgatac cgcgagaccc acgctcaccg gctccagatt tatcagcaat    5220
aaaccagcca gccggaaggg ccgagcgcag aagtggtcct gcaactttat ccgcctccat    5280
ccagtctatt aattgttgcc gggaagctag agtaagtagt tcgccagtta atagtttgcg    5340
caacgttgtt gccattgcta caggcatcgt ggtgtcacgc tcgtcgtttg gtatggcttc    5400
attcagctcc ggttcccaac gatcaaggcg agttacatga tcccccatgt tgtgcaaaaa    5460
agcggttagc tccttcggtc ctccgatcgt tgtcagaagt aagttggccg cagtgttatc    5520
actcatggtt atggcagcac tgcataattc tcttactgtc atgccatccg taagatgctt    5580
ttctgtgact ggtgagtact caaccaagtc attctgagaa tagtgtatgc ggcgaccgag    5640
ttgctcttgc ccggcgtcaa tacgggataa taccgcgcca catagcagaa ctttaaaagt    5700
gctcatcatt ggaaaacgtt cttcggggcg aaaactctca aggatcttac cgctgttgag    5760
atccagttcg atgtaaccca ctcgtgcacc caactgatct tcagcatctt ttactttcac    5820
cagcgtttct gggtgagcaa aacaggaag gcaaaatgcc gcaaaaaagg gaataagggc    5880
gacacggaaa tgttgaatac tcatactctt cctttttcaa tattattgaa gcatttatca    5940
gggttattgt ctcatgagcg gatacatatt tgaatgtatt tagaaaaata aacaaatagg    6000
ggttccgcgc acatttcccc gaaaagtgcc acctgacgtc taagaaacca ttattatcat    6060
gacattaacc tataaaaata ggcgtatcac gaggcccttt cgtcggcgcg ccgcggcc     6118
```

```
<210> SEQ ID NO 5
<211> LENGTH: 13
<212> TYPE: PRT
<213> ORGANISM: Artificial
<220> FEATURE:
<223> OTHER INFORMATION: synthesized

<400> SEQUENCE: 5

Ala Ala Cys Ser Ser Ser Pro Ser Lys His Cys Gly Gly
1               5                   10

<210> SEQ ID NO 6
<211> LENGTH: 15
<212> TYPE: PRT
<213> ORGANISM: Artificial
<220> FEATURE:
<223> OTHER INFORMATION: synthesized

<400> SEQUENCE: 6

Gly Gly Gly Gly Ser Gly Gly Gly Gly Ser Gly Gly Gly Gly Ser
1               5                   10                  15

<210> SEQ ID NO 7
<211> LENGTH: 20
<212> TYPE: DNA
<213> ORGANISM: Artificial
<220> FEATURE:
<223> OTHER INFORMATION: synthesized

<400> SEQUENCE: 7
gcacgattca gcaagcaagg                                                   20
```

```
<210> SEQ ID NO 8
<211> LENGTH: 26
<212> TYPE: DNA
<213> ORGANISM: Artificial
<220> FEATURE:
<223> OTHER INFORMATION: synthesized

<400> SEQUENCE: 8
cggtacctct acctatttga gttttg                                              26
```